(12) United States Patent
Li et al.

(10) Patent No.: US 9,364,529 B2
(45) Date of Patent: *Jun. 14, 2016

(54) TRUNCATED L1 PROTEIN OF HUMAN PAPILLOMAVIRUS TYPE 18

(75) Inventors: Shaowei Li, Fujian (CN); Wentong Shen, Fujian (CN); Zhongyi Li, Fujian (CN); Minghui Xie, Fujian (CN); Huirong Pan, Fujian (CN); Ningshao Xia, Fujian (CN)

(73) Assignees: Beijing Wantai Biological Pharmacy Enterprise Co., Ltd., Beijing (CN); Xiamen University, Xiamen (CN)

( * ) Notice: Subject to any disclaimer, the term of this patent is extended or adjusted under 35 U.S.C. 154(b) by 1093 days.

This patent is subject to a terminal disclaimer.

(21) Appl. No.: 12/598,187

(22) PCT Filed: Apr. 29, 2008

(86) PCT No.: PCT/CN2008/000873
§ 371 (c)(1),
(2), (4) Date: Jun. 14, 2010

(87) PCT Pub. No.: WO2008/134935
PCT Pub. Date: Nov. 13, 2008

(65) Prior Publication Data
US 2010/0272751 A1    Oct. 28, 2010

(30) Foreign Application Priority Data

Apr. 29, 2007 (CN) ........................... 2007 1 0097763
Jan. 23, 2008 (CN) ........................... 2008 1 0008731

(51) Int. Cl.
| A61K 39/12 | (2006.01) |
| C07K 14/005 | (2006.01) |
| C12N 7/00 | (2006.01) |
| A61K 39/00 | (2006.01) |

(52) U.S. Cl.
CPC .............. *A61K 39/12* (2013.01); *C07K 14/005* (2013.01); *C12N 7/00* (2013.01); *A61K 2039/5258* (2013.01); *A61K 2039/55566* (2013.01); *A61K 2039/70* (2013.01); *C12N 2710/20011* (2013.01); *C12N 2710/20022* (2013.01); *C12N 2710/20023* (2013.01); *C12N 2710/20034* (2013.01)

(58) Field of Classification Search
CPC ............... A61K 2039/5258; C07K 14/005; C07K 2319/00; C07K 2319/735; C12N 2710/20034; C12N 15/62; C12N 2710/20022; C12N 2710/20023; C12N 2710/20011; C12N 15/1017
See application file for complete search history.

(56) References Cited

U.S. PATENT DOCUMENTS

| 5,820,870 A | 10/1998 | Joyce et al. |
| 5,840,306 A | 11/1998 | Hofmann et al. |
| 5,866,553 A | 2/1999 | Donnelly et al. |
| 6,013,262 A | 1/2000 | Frazer et al. |
| 6,066,324 A | 5/2000 | Gissmann et al. |
| 6,551,597 B1 | 4/2003 | Harrison et al. |
| 6,599,508 B1 | 7/2003 | Gissmann et al. |
| 6,602,697 B1 | 8/2003 | Cook, III |
| 6,649,167 B2 | 11/2003 | Hallek et al. |
| 6,908,615 B1 | 6/2005 | Hofmann et al. |
| 7,351,533 B2 | 4/2008 | McCarthy et al. |
| 7,709,010 B2 | 5/2010 | Bryan et al. |
| 7,754,430 B2 | 7/2010 | Gissmann et al. |
| 2002/0193565 A1* | 12/2002 | Stanley et al. ................. 530/350 |
| 2003/0118609 A1 | 6/2003 | Harrison et al. |
| 2004/0081661 A1 | 4/2004 | Hallek et al. |
| 2004/0202679 A1 | 10/2004 | Gissmann et al. |
| 2005/0031636 A1 | 2/2005 | Gissman et al. |
| 2005/0175632 A1 | 8/2005 | Wettendorff |
| 2006/0153864 A1 | 7/2006 | Gissmann et al. |
| 2006/1098853 | 9/2006 | Gissmann et al. |
| 2007/0036824 A1 | 2/2007 | Bryan et al. |
| 2007/0224218 A1 | 9/2007 | Wettendorff |
| 2008/0248062 A1 | 10/2008 | Bryan et al. |
| 2008/0279890 A1 | 11/2008 | Wettendorff |
| 2009/0028894 A1 | 1/2009 | Gissmann et al. |
| 2010/0255031 A1 | 10/2010 | Gu et al. |
| 2010/0272751 A1 | 10/2010 | Li et al. |
| 2010/0291141 A1 | 11/2010 | Zhang et al. |

FOREIGN PATENT DOCUMENTS

| CN | 1185176 | 6/1998 |
| CN | 1478790 | 3/2004 |
| CN | 1578787 | 2/2005 |
| CN | 1642571 | 7/2005 |
| CN | 1683010 | 10/2005 |
| CN | 1821410 | 8/2006 |
| CN | 200710097762.8 | 4/2007 |
| CN | 200710097763.2 | 4/2007 |

(Continued)

OTHER PUBLICATIONS

Chen et al., "Papillomavirus capsid protein expression in *Escherichia coli*: purification and assembly of HPV11 and HPV16 L1," *Journal of Molecular Biology*, vol. 307, No. 1, pp. 173-182, Mar. 16, 2001.
Cole et al., "Nucleotide sequence and comparative analysis of the human papillomavirus type 18 genome—Phylogeny of papillomaviruses and repeated structure of the E6 and E7 gene products," *Journal of Molecular Biology*, vol. 193, No. 4, pp. 599-608, Feb. 20, 1987.
European Search Report; Application No. 08748432.5—2406; mailed Dec. 23, 2011 (9 pages).
Chen et al., "Structure of Small Virus-Like Particles Assembled from the L1 protein of Human Papillomavirus 16," Molecular Cell 5:557-567, 2000.
International Search Report; Application No. PCT/CN2008/000873; mailed Aug. 14, 2008; 7 pages.
International Search Report (in Chinese); Application No. PCT/CN2008/000872; 22 pages.
Cheng et al., "Construction of Recombinant Plasmid pQE32-HPV18 L1 and Protein Expression," Chinese Journal of Nosocomiology, Aug. 2005, vol. 15, No. 8, pp. 845-848.
EMBL Database, Accession No. Q80B70, Jun. 1, 2003.
European Communication; Application No. 08748431.7-1405; mailed Feb. 14, 2013; 7 pages.

(Continued)

*Primary Examiner* — Bao Li
(74) *Attorney, Agent, or Firm* — Fish & Richardson P.C.

(57) ABSTRACT

The invention relates to a truncated L1 protein of the Human Papillomavirus Type 18, a virus-like particle consisting of the protein, a vaccine comprising said virus-like particle, and the use of the vaccine in the prevention of cervical cancer.

16 Claims, 6 Drawing Sheets

(56) References Cited

FOREIGN PATENT DOCUMENTS

| | | |
|---|---|---|
| CN | 200810008731.5 | 1/2008 |
| CN | 200810008761.6 | 1/2008 |
| CN | 101153 280 | 4/2008 |
| CN | 101153280 | 4/2008 |
| EP | 2 147 926 | 1/2010 |
| WO | 94/20137 | 9/1994 |
| WO | WO 00/54730 | 9/2000 |
| WO | WO 02/43757 | 6/2002 |
| WO | WO 03/018624 | 3/2003 |
| WO | WO 03/077942 | 9/2003 |
| WO | WO 03/078455 | 9/2003 |
| WO | 03/093437 | 11/2003 |
| WO | 2004/056389 | 7/2004 |
| WO | WO 96/2941 | 9/2006 |
| WO | 2008/134934 | 11/2008 |
| WO | WO 2008/134935 | 11/2008 |

OTHER PUBLICATIONS

European Office Action; Application No. 08748432.5-2406; mailed Nov. 27, 2012; Applicant: Beijing Wantai Biological Pharmacy Enterprise Co., Ltd., 6 pages.
European Search Report; Application No. 08748431.7-1223 / 2154147; mailed Oct. 4, 2011; (9 pages).
Janine T. Bryan, "Developing an HPV Vaccine to Prevent Cervical Cancer and Genital Warts," Vaccine 28:3001-3006, 2007.
Bishop B et al., "Structure-based engineering of papillomavirus major capsid L1: controlling particle assembly," Virol J. Jan. 8, 2007;4:3, 6 pgs.
Brief Communication issued in EP 08748431.7 on Dec. 9, 2013 (1 page).
Caparros-Wanderley et al., "Intratype Sequence Variation Among Clinical Isolates of the Human Papillomavirus Type 6 L 1 ORF: Clustering of Mutations and Identification of a Frequent Amino Acid Sequence Variant"; Journal of General Virology, Apr. 1999; vol. 80, pp. 1025-1033.
Chen XS, Casini G, Harrison SC, Garcea RL. Papillomavirus capsid protein expression in Escherichia coli: purification and assembly of HPV11 and HPV16 L 1. J Mol Biol. Mar. 16, 2001;307(1):173-82.
Cho HJ, Oh YK, Kim VB. Advances in human papilloma virus vaccines: a patent review. Expert Opin Ther Pat. Mar. 2011;21(3):295-309. Epub Jan. 21, 2011.
Dartmann K, Schwarz E, Gissmann L, zur Hausen H. The nucleotide sequence and genome organization of human papilloma virus type 11. Virology May 1986;151(1):124-30.
Fang et al., "Post translational modifications of recombinant human Papillomavirus type 6b major capsid protein," Virus Research, 60(2):113-121 (1999).
Final Office Action issued in U.S. Appl. No. 12/598,186 on Jun. 5, 2013 (12 pages).
Final Office Action issued in U.S. Appl. No. 12/601,972 on Aug. 21, 2012 (8 pages).
Jana et al., "Strategies for efficient production of heterologous proteins in Escherichia coli," Applied Microbiology and Biotechnology, 67(3):289-298 (2005).
Kelsall et al., "Expression of the Major Capsid Protein of Human Papillomavirus Type 16 in Escherichia Coli," Journal of Virological Methods, Elsevier, BV, NL, 53(1) (1995).
Luo et al., "Construction and application of an Escherichia coli high effective expression vector with an enhancer," Chinese Journal of Biotechnology, 16(5):578-581 (2000) (with English translation of Abstract).
Neeper et. al. HPV6 protein coding sequence. NCBI—GenBank. Acc. # AAC53712; submitted Apr. 19, 1996 (1 page).
Office Action issued in EP 08748431.7 on Dec. 5, 2013 (12 pages).
Office Action issued in U.S. Appl. No. 12/598,186 on Nov. 21, 2012 (6 pages).
Office Action issued in U.S. Appl. No. 12/601,972 on Feb. 15, 2012 (8 pages).
Office Action issued in U.S. Appl. No. 12/601,972 on May 23, 2013 (23 pages).
RCE and Response to Final Office Action issued in U.S. Appl. No. 12/601,972 on Aug. 21, 2012 filed Feb. 20, 2013 (17 pages).
RCE and Response to Final Office Action issued in U.S. Appl. No. 12/598,186 on Jun. 5, 2013 filed Dec. 5, 2013 (12 pages).
Response to Office Action issued in U.S. Appl. No. 12/601,972 on Feb. 15, 2012 filed Jun. 14, 2012 (10 pages).
Response to Office Action issued in U.S. Appl. No. 12/601,972 on May 23, 2013 filed Nov. 25, 2013 (21 pages).
Response to Office Action issued in U.S. Appl. No. 12/598,186 on Nov. 21, 2012 filed Apr. 18, 2013 (9 pages).
Response to Restriction Requirement issued in U.S. Appl. No. 12/601,972 on Nov. 4, 2011 filed Feb. 1, 2012 (8 pages).
Response to Restriction Requirement issued in U.S. Appl. No. 12/598,186 on Sep. 25, 2012 filed Oct. 25, 2012 (1 page).
Restriction Requirement issued in U.S. Appl. No. 12/601,972 on Nov. 4, 2011 (7 pages).
Restriction Requirement issued in U.S. Appl. No. 12/598,186 on Sep. 25, 2012 (8 pages).
Schiller JT, Castellsague X, Garland Sm. A review of clinical trials of human papillomavirus prophylactic vaccines. Vaccine. Nov. 20, 2012;30 Suppl 5:F123-38.
Supplemental Response to Final Office Action issued in U.S. Appl. No. 12/601,972 on Aug. 21, 2012, filed Apr. 1, 2013 (20 pages).
Wang, Jiabi et al., "Expression of Recombinant HPV6 L 1 Protein in Prokaryotic System," Journal Clinical Dermatol, Jun. 2003, vol. 32, No. 6, ISSN 1000-4963.
Bonnez et al., "Evolution of the antibody response to human papillomavirus type 11 (HPV-11) patients with condyloma acuminatum according to treatment response," J Med Virol., 1993, 39(4):340-344.
European Search Report corresponding to EP Application No. 08757380.4 dated Mar. 12, 2010.
European Office Action for Appln. No. 08 757 380.4 dated May 15, 2013, 5 pages.
European Search Report in Application No. 08757381.2 dated Jan. 27, 2014, 4 pages.
European Search Report in Application No. 08757381.2 dated Mar. 9, 2011, 5 pages.
Final office action issued in U.S. Appl. No. 12/601,972 on Feb. 27, 2014 (19 pages).
Li et al., "Expression of human papillomavirus type 11 L1 capsid protein in Escherichia coli: characterization of protein domains involved in DNA binding and capsid assembly," J Virol., Apr. 1997, 71(4):2988-95.
Ma et al., "Increasing the expression levels of papillomavirus major capsid protein in Escherichia coli by N-terminal deletion," Protein Expression and Purification, 2007, 56:72-79.
Office Action issued in U.S. Appl. No. 12/598,186 on Feb. 20, 2014 (7 pages).
Office Action issued in U.S. Appl. No. 12/601,983, dated Oct. 1, 2012, 8 pages.
Office Action issued in U.S. Appl. No. 12/601,983, dated Mar. 14, 2013, 11 pages.
Response to Office Action issued in U.S. Appl. No. 12/601,983 on Oct. 1, 2012 filed Feb. 6, 2013 (10 pages).
Response to Restriction Requirement issued in U.S. Appl. No. 12/601,983 on Jul. 6, 2012, filed Aug. 6, 2012 (7 pages).
Restriction Requirement issued in U.S. Appl. No. 12/601,983 on Jul. 6, 2012 (8 pages).
Rose et al., "Expression of human papillomavirus type 11 L1 protein in insect cells in-vivo and in-vitro assembly of viruslike particles," J Virol., Apr. 1993, 67(4):1936-1944.
Terminal Disclaimer in U.S. Appl. No. 12/601,983, filed Feb. 21, 2014, 1 page.
Villa et al , "Immunologic responses following administration of a vaccine targeting human papillomavirus Types 6, 11, 16 and 18," Vaccine, Jul. 7, 2006, 24(27-28):5571-83.
Written Opinion of International Searching Authority for PCT/CN2008/001050, English version, dated Sep. 11, 2009.
Xu et al., "Transformation activity 1-6 and the immunogenicity of a human papillomavirus type 16 variant E6E7 gene from cervical carcinoma biopsy in Shandong province," Xhonghua Weishengwuxue He Mianyixue Zazhi, Jul. 4, 2002, 22(4):427-432 (English Abstract).

(56) References Cited

OTHER PUBLICATIONS

Yan et al., "Expression, purification and immunogenicity of human papillomavirus type 11 virus-like particles from *Excherichia coli*," Weshengwu Xuebao, Nov. 2009, 49(11):1527-1533 (English Abstract).

Zhuang et al., "Construction and Identification of Prokaryotic Expression System with L1 Gene of Human Papillomavirus Type 11," Chinese J Endemiol., Mar. 20, 2004, 23(2):163-165 (English Abstract).

Appeal Brief filed in U.S. Appl. No. 12/601,983, filed Apr. 16, 2014, 17 pages.

Office Action issued in U.S. Appl. No. 12/598,186, dated Sep. 17, 2014, 11 pages.

Response to Office Action issued in U.S. Appl. No. 12/598,186 on Feb. 20, 2014, filed Aug. 20, 2014, 6 pages.

RCE and Response to Office Action issued in U.S. Appl. No. 12/598,186, dated Sep. 17, 2014, filed Jan. 20, 2015, 10 pages.

Office Action issued in U.S. Appl. No. 12/601,983 dated Aug. 28, 2014, 14 pages.

GenBank: AAA46935.1. major capsid protein [Human papillomavirus type 11], Jun. 4, 1994. http://www.ncbi.nlm.nih.gov/protein/496201.

GenBank: AAQ92369.1, HPV18 major capsid protein L 1 [synthetic construct], Oct. 11, 2003 http://www.ncbi.nlm.nih.gov/protein/375288783?report=genbank&log$=protalign&blast_rank=1&RID=V8ACF90G015.

GenBank: AAC80442.1, major capsid protein [Human papillomavirus type 6], Apr. 13, 1999 http://www.ncbi.nlm.nih.gov/protein/3930543?report=genbank&log$=protalign&blast_rank=1&RID=V88RAMAW014.

GenBank: AAC09292.1, late major capsid protein [Human papillomavirus type 16], Apr. 2, 1998 http://www.ncbi.nlm.nih.gov/protein/3005059?report=genbank&log$=protalign&blast_rank=4&RI.

Response to Office Action issued in U.S. Appl. No. 12/601,983 on Aug. 28, 2014, filed Dec. 23, 2014 (6 pages).

Dwyer et al., "Computational Design of a Biologically Active Enzyme," Science, 304(5679):1967-1971 (Jun. 2004).

European Office Action issued in EP08757380.4-1405 dated Oct. 20, 2014 (3 pages).

Fey et al., "Demonstration of In Vitro Synthesis of Human Papilloma Viral Proteins from Hand and Foot Warts," J. Invest. Dermatol., 92:817-824 (1989).

Final Office Action issued in U.S. Appl. No. 12/601,983 on Feb. 13, 2015 (10 pages).

Murby et al., "Hydrophobicity Engineering to Increase Solubility and Stability of a Recombinant Protein from Respiratory Syncytial Virus," European Journal of Biochemistry, 230(1):38-44 (May 1995).

Nygren et al., "Engineering proteins to facilitate bioprocessing," Trends in Biotechnology, Elsevier Publications, Cambridge, GB, 12(5):184-188 (May 1994).

Office Action issued in EP08748432.5 on Feb. 5, 2015 (10 pages).

Request Under AFCP and Response to Final Office Action issued in U.S. Appl. No. 12/601,983 on Feb. 13, 2015, filed Apr. 13, 2015 (8 pages).

Response to Restriction Requirement issued in U.S. Appl. No. 14/248,063 on Jan. 21, 2015 filed Mar. 23, 2015 (2 pages).

Restriction Requirement issued in U.S. Appl. No. 14/248,063 on Jan. 21, 2015 (6 pages).

Schein et al., "Deletions at the C-terminus of Interferon Gamma Reduce RNA Binding and Activation of Double-Stranded-RNA cleavage by Bovine Seminal Ribonuclease," Biochemical Journal, 307(1):123-127 (1995).

Sterner, R., "Biochemistry: De Novo Design of an Enzyme," Science, 304(5679):1916-1917 (Jun. 2004).

GE Healthcare, "Purifying Challenging Proteins: Principles and Methods," https://www.mcdb.ucla.edu/Research/Jacobsen/LabWebSite/PDFOthers/GESeminar.pdf, 2007, pp. 1-33.

Office Action issued in U.S. Appl. No. 14/601,983 on May 13, 2015 (10 pages).

Office Action issued in U.S. Appl. No. 14/248,063 on Jun. 10, 2015 (21 pages).

Casini et al., "In vitro papillomavirus capsid assembly analyzed by light scattering," Virology, 325(2):320-327 (Aug. 1, 2004).

Chen et al., "Structure of small virus-like particles assembled from the L1 protein of human papillomavirus 16," Molecular Cell, 5(3):557-567 (Mar. 1, 2000).

European Search Report dated Jul. 22, 2015 for Appln. No. 15160399.0 (8 pages).

European Search Report dated Jul. 27, 2015 for Appln. No. 15160363.6 (11 pages).

Indian Office Action dated Jul. 27, 2015 for Appln. No. 8058/DELNP/2009.

Kelsall et al., "Expression of the major capsid protein of human papillomavirus type 16 in *Escherichia coli*," Journal of Virological Methods, 53(1):75-90 (Jan. 1, 1995).

Li et al., "Expression of the human papillomavirus type 11 L1 capsid protein in *Escherichia coli*: characterization of protein domains involved in DNA binding and capsid assembly," Journal of Virology, The American Society for Microbiology, 71:2988-2995 (Apr. 1, 1997).

Neeper et al., "Expression of the major capsid protein of human papillomavirus type 11 in *Saccharomyces cerevisae*," Gene, 180(1-2):1-6 (Nov. 21, 1996).

Office Action issued in U.S. Appl. No. 12/601,983 on Sep. 8, 2015 (10 pages).

Response to Office Action issued in U.S. Appl. No. 14/248,063 on Jun. 10, 2015 filed on Sep. 29, 2015 (15 pages).

Xu et al., "Papillomavirus virus-like particles as vehicles for the delivery of epitopes or genes," Archives of Virology, 151(11):2133-2148 (Jun. 22, 2006).

Zhang et al., "Expression of human papillomavirus type 16 L1 protein in *escherichia coli*: denaturation, renaturation, and self-assembly of virus-like particles in vitro," Virology, 243(2):423-431 (Apr. 10, 1998).

U.S. Appl. No. 14/248,063, filed Apr. 8, 2014, Shaowei Li.

Office Action issued in U.S. Appl. No. 12/598,186 on Nov. 18, 2015 (5 pages).

Response to Office Action issued in U.S. Appl. No. 12/598,186 on Nov. 18, 2015 filed on Jan. 7, 2016 (11 pages).

Response to Office Action issued in U.S. Appl. No. 12/601,983 on Sep. 8, 2015, filed on Dec. 4, 2015 (6 pages).

Final Office Action issued in U.S. Appl. No. 14/248,063 on Jan. 6, 2016 (18 pages).

European Molecular Biology Laboratory (EMBL), "Extraction and Clarification: Preparation of cell lysates from *E. Coli*," https://www.embl.de/pepcore/pepcore_services/protein_purification/extraction_clarification/cell/lysates_ecoli/enzymatic_lysis/, accessed Dec. 30, 2015, Available online Feb. 1, 2002.

McCarthy et al., "Quantitative disassembly and reassembly of human papillomavirus type 11 viruslike particles in vitro," J. Virol., 72(1):32-41 (1998).

Final Office Action issued in U.S. Appl. No. 12/601,983 on Dec. 22, 2015 (10 pages).

\* cited by examiner

TRUNCATED L1 PROTEIN OF HUMAN PAPILLOMAVIRUS TYPE 18

FIELD OF THE INVENTION

The invention relates to a truncated L1 protein of the Human Papillomavirus Type 18, a virus-like particle consisting of the protein, a vaccine formulation comprising said virus-like particle, and the use of the vaccine in the prevention of cervical cancer.

BACKGROUND OF THE INVENTION

The human papillomavirus, a non-enveloped, deoxyribonucleic acid (DNA) virus, belongs to the genus of papovaviridae. The viral genome is a closed circle, double-stranded DNA, which is approximately 7.2-8 kb in length and contains 8 open reading frames (ORFs). The genome can be divided into three parts in terms of function: (1) the early region (E), approximately 4.5 Kb in length, coding for 6 non-structural proteins E1, E2, E4~E7 associated with virus replication, transcription and transformation; (2) the late region (L), approximately 2.5 Kb in length, coding for the major capsid protein L1 and the minor capsid protein L2; (3) the long control region (LCR), located between the end of the L region and the initiating terminal of the E region, approximately 800-900 bp in length, and comprising regulator elements for DNA replication and expression instead of coding for proteins. Viral particles are 45-55 nm in diameter, wherein the nucleocapsid, consisting of L1 and L2, exhibits icosahedral symmetry and comprise 72 capsomers.

Currently, there are over 90 different types of HPV, mainly causing papillary disease in the skin and mucosa of human. HPV types are divided into three groups depending on their relation with tumorigenesis: (1) group of low or no cancerogenic risk, containing types 6, 11, 39, 41, 42, and 43; (2) group of medium cancerogenic risk, containing types 31, 33, 35, 51, and 52; and (3) group of high cancerogenic risk, containing types 16, 18, 45, and 56.

Molecular epidemiological investigation on HPV suggests that infection caused by high-risk HPV types is a principle factor in the development of cervical cancer. HPV DNA are detected with over 80% positivity rate in all cases of cervical cancer, about 60% for HPV16 and about 15% for HPV18 (Clifford, G., S. Franceschi, et al. Vaccine 2006.24 Suppl 3:S26-34).

Cervical cancer is the second most common malignant tumor among women, following breast cancer, and seriously threatens the health of women. There are about 490,000 newly reported cases worldwide every year, and nearly 270,000 people die of this disease annually (Boyle, P., and J. Ferlay. Ann Oncol 2005, 16:481-8). Cases in developing countries account for approximately 83% of the total, and about 15% of these involve malignant neoplasms, in contrast to 1.5% in developed countries. Cervical cancer is most prevalent in sub-Saharan Africa, Latin America, and Southern and Eastern Asia. Cervical cancer is also prevalent in China. The incidence of cervical cancer among married women is as high as 1026/100000 in Lueyang County of Shanxi Province. Therefore, a safe and effective HPV vaccine, especially against high-risk types such as HPV 16 and 18, would be an effective way to prevent cervical cancer and improve health of women.

HPV L1 protein, with a molecular weight of 55-60 kDa, is the major capsid protein of the human papillomavirus and the main target protein of the HPV vaccine. HPV L1 protein expressed in multiple different expression systems can form Virus-like particles (VLPs) which resemble native HPV particles morphologically, without the assistance of the L2 protein. The VLP, consisting of 72 pentamers of the L1 proteins, exhibits icosahedral symmetry. Since the VLPs retain the native epitopes of the viral particles, they are highly immunogenic and can induce the generation of neutralizing antibodies against homologous HPV (Kimbauer, R., F. Booy, et al. 1992 Proc Natl Acad Sci USA 89(24): 12180-4). Furthermore, the VLPs are safe and have no potential cancergenic risk as they contain no viral DNA. Therefore, VLP vaccines become the primary candidate for an HPV vaccine.

The key for development of a vaccine is to efficiently produce VLP vaccines of HPV in large-scale. Currently, the most commonly used expression systems are eukaryotic expression systems and prokaryotic expression systems.

The commonly used eukaryotic systems comprise poxvirus, insect baculovirus and yeast vectors. HPV L1 protein expressed in eukaryotic systems shows little conformational difference from that of the native virus, and can self-assemble into VLPs. Thus, purified VLPs can be easily obtained after gradient density centrifugation. It brings a lot of convenience to the purification work. However, due to the high culture costs and low expression level, it is quite difficult to product industrially on a large-scale. The HPV vaccine Gardasil®, which came into the market recently, is more expensive than others due to low expression level and high production cost of the *Saccharomyces cerevisiae* expression system employed in its manufacture.

The expression of HPV L1 protein in a prokaryotic system such as *E. coli* has been previously reported. Banks, Matlashewski, et al. published a paper regarding the expression of HPV 16 L1 by employing *E. coli* (Banks, L., G. Matlashewski, et al. (1987). J Gen Virol 68 (Pt 12): 3081-9). However, most HPV L1 proteins expressed by *E. coli* lose their native conformation and cannot induce the generation of protective antibodies against HPV. Alternatively, although HPV VLPs can be obtained from the incorrectly folded proteins by steps such as purification from inclusion bodies and refolding, it is difficult to apply this method to large-scale production, as the protein is largely lost during the refolding process and the yield is low (Kelsall, S. R. and J. K. Kulski (1995). J Virol Methods 53(1): 75-90). Although HPV L1 protein may be expressed in a soluble form with a correct conformation in *E. coli* and dissolved in the supernatants of *E. coli* lysate, the expression level is low. Moreover, since there are large number and amount of impure proteins, it is difficult to isolate the proteins of interest from them. Although it is resported that the expression level of L1 protein can be increased in the supernatants by means of GST fusion expression and the purification of the protein of interest is facilitated (Li, M., T. P. Cripe, et al. (1997), J Virol 71(4): 2988-95), it still cannot be applied to large-scale production because expensive enzymes are required to cleave the fusion protein.

Therefore, a HPV L1 protein capable of inducing the generation of protective antibodies against HPV, and a virus-like particle consisting of the same are still needed in the art, so that it is possible to produce vaccines for cervical cancer industrially on a large scale.

DESCRIPTION OF THE INVENTION

This invention aims to provide a novel HPV type 18 L1 protein, the VLPs consisting of it, and a vaccine comprising the VLPs.

During research, it was found by chance that the *E. coli* expression system can produce a truncated HPV 18 L1 protein that can induce the generation of neutralizing antibodies against HPV 18. After purification, the truncated HPV 18 L1 protein can be produced in high yield, with at least 50% purity. Further treatment of the purified HPV L1 protein can produce VLPs, which can induce the production of neutralizing antibodies. The invention has been completed based on the above.

Therefore, the first aspect of the invention relates to HPV 18 L1 proteins with 50, 55, 60, 65, or 70 amino acids truncated at N-terminal as compared to a wild type HPV 18 L1 protein. Preferably, the truncated protein has the sequence set forth in SEQ ID Nos:1, 2, 3, 4, or 5, especially the sequence set forth in SEQ ID NO:1.

A further aspect of the invention relates to a polynucleotide encoding the truncated protein according to the invention, and a vector containing the polynucleotide.

A further aspect of the invention relates to a cell comprising the vector.

The invention also relates to a composition comprising the truncated protein, the polynucleotide, the vector, or the cell.

A further aspect of the invention relates to a HPV 18 VLP, comprising or consisting of HPV 18 L1 proteins with 50, 55, 60, 65, or 70 amino acids truncated at the N terminal such as HPV 18 L1 proteins having a sequence set forth in SEQ ID NOs: 1, 2, 3, 4 or 5.

A further aspect of the invention relates to a method for obtaining the HPV 18 L1 protein, comprising the expression of a truncated HPV 18 L1 gene fragment in an *E. coli* system and the subsequent purification of the protein from the lysate supernatant.

In a preferred embodiment of the invention, a method for obtaining HPV 18 L1 protein comprises:
  a) expressing the truncated HPV 18 L1 gene fragment in a *E. coli* expression system;
  b) disrupting *E. coli*, which has expressed the truncated HPV 18 L1 protein, in a salt solution at a concentration of from 100 mM to 600 mM, and isolating the supernatant;
  c) decreasing the salt concentration of the supernatant in b) to from 100 mM to 0, inclusive, by using water or a low salt solution, and collecting a precipitate;
  d) redissolving the precipitation in c) in a salt solution at a concentration of from 150 mM to 2500 mM, with a reductant added, and then isolating the resultant solution, wherein the solution contains the truncated HPV 18 L1 protein with a purity of at least 50%.

More generally, the invention also relates to a method for obtaining a HPV L1 protein, such as the HPV 18 L1 protein according to the invention, comprising:
  a) expressing the HPV L1 gene encoding HPV L1 protein in an *E. coli* expression system;
  b) disrupting *E. coli*, which has expressed the HPV L1 protein, in a salt solution at a concentration of from 100 mM to 600 mM, and isolating the supernatant;
  c) decreasing the salt concentration of the supernatant in b) to from 100 mM to 0, inclusive, by using water or a low salt solution, and collecting a precipitate;
  d) redissolving the precipitation of c) in a salt solution at a concentration of from 150 mM to 2500 mM, with a reductant added, and then isolating the resultant solution, wherein the solution contains the HPV L1 protein with a purity of at least 50%.

The invention also relates to a vaccine for the prevention of cervical cancer, comprising VLPs of HPV 18 L1 proteins according to the invention, preferably in an amount effective to prevent cervical cancer. Preferably, the vaccine further comprises at least one VLP of HPV16, 11, 6, 31, 33, 45, 52, or 58 L1 proteins, preferably in an amount effective to prevent cervical cancer or infection caused by the corresponding HPV types. Generally, the vaccine further contains excipients or vectors for vaccine.

Preferably, the vaccine comprises HPV 16 VLPs and HPV 18 VLPs, especially the HPV 16 VLPs comprising or consisting of the protein having the amino acid sequence set forth in SEQ ID No: 7, and the HPV 18 VLPs comprising or consisting of the protein having the amino acid sequence set forth in SEQ ID No: 1. More preferably, the vaccine further comprises HPV 6 VLPs and HPV 11 VLPs, especially the HPV 6 VLPs comprising or consisting of the protein having the amino acid sequence set forth in SEQ ID No: 8, and the HPV 11 VLPs comprising or consisting of the protein having the amino acid sequence set forth in SEQ ID No: 9.

In a specially preferred embodiment, the vaccine comprises the HPV 16 VLPs comprising or consisting of the protein having the amino acid sequence set forth in SEQ ID No: 7, the HPV 18 VLPs comprising or consisting of the protein having the amino acid sequence set forth in SEQ ID No: 1, the HPV 6 VLPs comprising or consisting of the protein having the amino acid sequence set forth in SEQ ID No: 8, and the HPV 11 VLPs comprising or consisting of the protein having the amino acid sequence set forth in SEQ ID No: 9, preferably, in an amount effective to prevent cervical cancer or infection caused by the corresponding HPV subtypes.

The invention further relates to the use of the HPV 18 L1 protein or the VLPs thereof in the manufacture of a vaccine for the prevention of cervical cancer.

The invention further relates to a method for preventing cervical cancer, comprising administrating a vaccine comprising an preventively effective amount of HPV 18 L1 protein to an individual in need of it.

The invention involves a method for obtaining VLPs of the HPV 18 L1 protein, comprising:
  e) further purifying the truncated HPV 18 L1 protein with a purity of at least 50% by subjecting it to a chromatography;
  f) removing the reductant from the HPV 18 L1 protein obtained in e).

This invention involves a method for preparing a vaccine for preventing cervical cancer, comprising blending the VLPs above, and optionally, one or more VLPs selected from the group consisting of VLPs of HPV 6, 11, 16, 31, 33, 45, 52 and 58, with vectors or excipients for vaccines.

DEFINITIONS OF THE TERM IN PRESENT INVENTION

According to the invention, the term "*E. coli* expression system" refers to a expression system consisting of *E. coli* (strains) and vectors, wherein the *E. coli* (strains) include, but are not limited to: GI698, ER2566, BL21 (DE3), B834 (DE3), and BLR (DE3), which are available on the market.

According to the invention, the term "vectors" refers to the nucleic acid carrier tools which have the polynucleotide encoding a certain protein inserted therein and allow for the expression of the protein. The "vector" can have the carried genetic material expressed in a host cell by transformation, transduction, and transfection into the host cell. For example, "vectors" include plasmids, phages, cosmids and the like.

According to the invention, the term "a gene fragment of the truncated HPV 18 L1 protein" refers to the nucleic acids with the nucleotide(s) encoding one or more amino acid sequences deleted at 5' or 3' terminal of the wild-type HPV 18 L1 gene (cDNA). The full-length gene sequence of the wild-type HPV 18 L1 gene can be found in, but not limited to, the following NCBI sequences: AY262282.1, X05015.1, AY863156.1 and U89349.1.

The term "truncated HPV 18 L1 protein" refers to the protein with one or more amino acids deleted at the N- and/or C-terminal of the wild-type HPV 18 L1 protein. The full-length gene sequence of the wild-type HPV 18 L1 protein can be found in, but not limited to, the full-length L1 proteins encoded by the following NCBI sequences: AY262282.1, X05015.1, AY863156.1 and U89349.1.

According to the invention, the term "excipients and vectors for vaccines" refers to one or more reagents, including but not limited to: pH regulators, surfactants, adjuvants, and ionic strength enhancers. For example, pH regulators include, but are not limited to, phosphate buffers; surfactants include, but are not limited to: anion surfactants, cation surfactants, non-ionic surfactants (for example, but not limited to Tween-80); adjuvants include, but are not limited to, aluminum hydroxide and Freund's complete adjuvant; and Ionic strength enhancers include, but are not limited to, NaCl.

According to the invention, the term "chromatography" includes, but is not limited to: ion exchange chromatography (e.g. cation-exchange chromatography), hydrophobic interaction chromatography, absorbant chromatography (e.g. hydroxyapatite chromatography), gel filtrate chromatography (gel exclusion chromatography), and affinity chromatography.

According to the invention, the truncated HPV 18 L1 proteins can be obtained preferably by the following steps:
a) disrupting *E. coli*, which expresses truncated HPV 18 L1 protein, in a buffer containing 100-600 mM salt, preferably 200-500 mM;
b) isolating the supernatant from the disrupted solution, then decreasing the salt concentration of the supernatant to 100 mM-0M with water or a low-salt buffer (generally, with a salt concentration lower than the one of the buffer for disrupting);
c) separating a precipitant from the supernatant with a salt concentration as low as 100 mM-0;
d) redissoving the precipitant in a solution containing a reductant and having a salt concentration of 150-2000 mM, preferably greater than 200 mM;
e) isolating a solution of the truncated HPV 18 L1 proteins with a purity of at least 50%, preferably at least 70%, more preferably at least 80%.

According to the invention, in the method for obtaining the truncated HPV 18 L1 proteins, the term "buffer" refers to a solution which can maintain pH value stable within a certain range, including but not limited to: Tris buffers, phosphate buffers, HEPES buffers, and MOPS buffers.

According to the invention, the disrupting of the prokaryotic host cell can be achieved by methods including, but not limited to one or more of homogenizer disrupting, ultrasonic treatment, grinding, high pressure extrusion, and lysozyme treatment.

According to the invention, in the method for obtaining the truncated HPV 18 L1 proteins, the salts used include, but are not limited to: one or more of neutral salts, especially alkali metal salt, ammonium salts, hydrochlorides, sulfates, bicarbonates, phosphate salts or hydrogenphosphates, especially NaCl, KCl, $NH_4Cl$, $(NH_4)_2SO_4$.NaCl are preferred. The reductant used includes, but is not limited to, DTT and 2-mercaptoethanol, in an amount of including, but not limited to, 10-100 mM.

According to the invention, the VLPs of the truncated HPV 18 L1 protein can be produced by the following steps: further purifying the truncated HPV 18 L1 protein with a purity of at least 50% by subjecting it to a chromatography, and thereby obtaining a purified truncated HPV 18 L1 protein solution; and removing the reductant from the purified HPV 18 L1 protein solution, and thereby obtaining the truncated HPV 18 L1 VLPs. Methods for removing the reductant include, but are not limited to, known techniques in the art, such as dialysis, ultrafiltration, and chromatography.

According to the invention, the truncated HPV L1 protein preferably has the sequence set forth in SEQ ID NO:1.

According to the invention, the vaccine can be administrated in a patient-accepted form, including but not limited to oral and injection, preferably injection.

According to the invention, the vaccine is preferably used in a unit dose. Each unit dose contains 5-80 μg truncated HPV 18 L1 VLP, preferably 20-40 μg.

Beneficial Effect

Presently, the expression systems useful for preparing HPV VLPs include eukaryotic and prokaryotic expression systems.

HPV L1 proteins expressed in eukaryotic expression systems retain their native conformation, and can form VLPs on their own. In most cases, VLP with a correct conformation can be obtained by simple purification. Nevertheless, eukaryotic expression systems, such as the baculovirus and yeast expression systems, are difficult to be applied in large-scale industrial production due to low expression levels and high costs.

Prokaryotic expression systems, such as *E. coli* systems, have the advantages of high expression levels at a lower cost. However, when expressed in a prokaryotic system, the HPV L1 protein usually loses its native conformation and is expressed in a form of inclusion bodies in the precipitant. Renaturation of the protein from inclusion bodies is still a problem worldwide. Due to the difficulty and inefficiency of renaturation, this method is limited to small-scale lab research and cannot be applied on a large scale so as to obtain VLP with a correct conformation from the inclusive bodies. Although the HPV L1 protein can exist in its native conformation in the supernatant of *E. coli* lysate, its expression levels are low. Moreover, it is quite difficult to purify the HPV L1 protein from the numerous soluble proteins in the *E. coli* lysate supernatant. Generally, the purification is completed by means such as fusion expression and affinity chromatography which are not feasible for industrial-scale processes due to expensive enzymes employed therein.

In this invention, N-truncated HPV 18 L1 protein is expressed in an *E. coli* expression system and is selectively precipitated from the *E. coli* lysate supernatant under mild conditions. The HPV L1 protein is then redissolved in a salt buffer to significantly improve its purity while still retaining its native conformation. The redissolved protein of interest can be immediately subjected to ion-exchange or hydrophobic interaction chromatography so as to obtain the pure protein. The purified, truncated HPV 18 L1 protein obtained from these steps, can self-assemble into VLPs with good immunogenicity and the ability to induce neutralizing antibodies of a high titer against HPV 18, which is a good vaccine for preventing human from HPV 18 infection. In addition, the truncated HPV 18 L1 protein used in the present invention is easily expressed in an *E. coli* expression system and can be economically purified without using expensive enzymes. Furthermore, because the protein of interest is not subjected to the intensive procedures of denaturation and renaturation during purification, the method can be applied industrially on a large scale due to low loss.

SEQUENCE LIST

Figure 1:
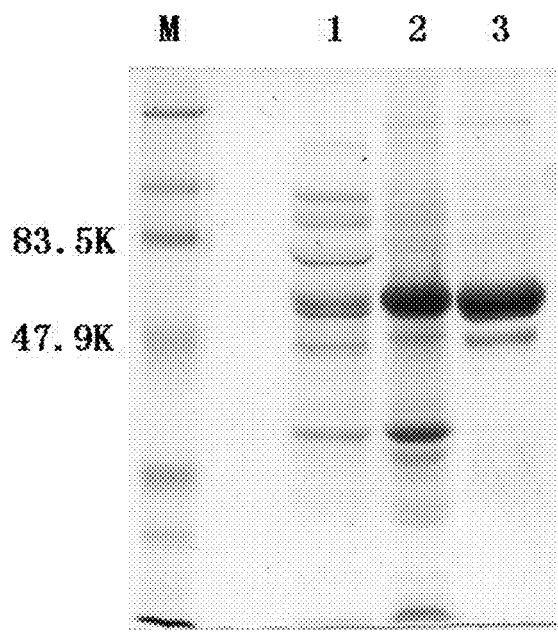
FIG. 1 shows the SDS-PAGE result of HPV18N65C-L1 protein in different phases during steps a)-d) of the method according to the invention. M: Molecular Weight Marker; Lane 1: Lysate supernatant 10 times diluted; Lane 2: HPV18N65C-L1 protein precipitated by tengenital flow; Lane 3: Redissolved HPV18N65C-L1 in a re-suspension solution. The electrophoretic result shows that the purity of HPV18N65C-L1 reached about 70% following the steps of precipitation and re-dissolution.

```
SEQ ID NO: 1:
  1 MRPSDNTVYL PPPSVARVVN TDDYVTRTSI FYHAGSSRLL TVGNPYFRVP AGGGNKQDIP

61 KVSAYQYRVF RVQLPDPNKF GLPDTSIYNP ETQRLVWACA GVEIGRGQPL GVGLSGHPFY

121 NKLDDTESSH AATSNVSEDV RDNVSVDYKQ TQLCILGCAP AIGEHWAKGT ACKSRPLSQG

181 DCPPLELKNT VLEDGDMVDT GYGAMDFSTL QDTKCEVPLD ICQSICKYPD YLQMSADPYG

241 DSMFFCLRRE QLFARHFWNR AGTMGDTVPQ SLYIKGTGMR ASPGSCVYSP SPSGSIVTSD

301 SQLFNKPYWL HKAQGHNNGV CWHNQLFVTV VDTTRSTNLT ICASTQSPVP GQYDATKFKQ

361 YSRHVEEYDL QFIFQLCTIT LTADVMSYIH SMNSSILEDW NFGVPPPPTT SLVDTYRFVQ

421 SVAIACQKDA APAENKDPYD KLKFWNVDLK EKFSLDLDQY PLGRKFLVQA GLRRKPTIGP

481 RKRSAPSATT ASKPAKRVRV RARK

SEQ ID NO: 2:
  1 MRNVNVFPIF LQMALWRPSD NTVYLPPPSV ARVVNTDDYV TRTSIFYHAG SSRLLTVGNP

61 YFRVPAGGGN KQDIPKVSAY QYRVFRVQLP DPNKFGLPDT SIYNPETQRL VWACAGVEIG

121 RGQPLGVGLS GHPFYNKLDD TESSHAATSN VSEDVRDNVS VDYKQTQLCI LGCAPAIGEH

181 WAKGTACKSR PLSQGDCPPL ELKNTVLEDG DMVDTGYGAM DFSTLQDTKC EVPLDICQSI

241 CKYPDYLQMS ADPYGDSMFF CLRREQLFAR HFWNRAGTMG DTVPQSLYIK GTGMRASPGS
```

```
301 CVYSPSPSGS IVTSDSQLFN KPYWLHKAQG HNNGVCWHNQ LFVTVVDTTR STNLTICAST

361 QSPVPGQYDA TKFKQYSRHV EEYDLQFIFQ LCTITLTADV MSYIHSMNSS ILEDWNFGVP

421 PPPTTSLVDT YRFVQSVAIT CQKDAAPAEN KDPYDKLKFW NVDLKEKFSL DLDQYPLGRK

481 PLVQAGLRRK PTIGPRKRSA PSATTSSKPA KRVRVRARK

SEQ ID NO: 3:
  1 MFPIFLQMAL WRPSDNTVYL PPPSVARVVN TDDYVTRTSI FYHAGSSRLL TVGNPYFRVP

61 AGGGNKQDIP KVSAYQYRVF RVQLPDPNKF GLPDTSIYNP ETQRLVWACA GVEIGRGQPL

121 GVGLSGHPFY NKLDDTESSH AATSNVSEDV RDNVSVDYKQ TQLCILGCAP AIGEHWAKGT

181 ACKSRPLSQG DCPPLELKNT VLEDGDMVDT GYGAMDFSTL QDTKCEVPLD ICQSICKYPD

241 YLQMSADPYG DSMFFCLRRE QLFARHFWNR AGTMGDTVPQ SLYIKGTGMR ASPGSCVYSP

301 SPSGSIVTSD SQLFNKPYWL HKAQGHNNGV CWHNQLFVTV VDTTRSTNLT ICASTQSPVP

361 GQYDATKFKQ YSRHVEEYDL QFIFQLCTIT LTADVMSYIH SMNSSILEDW NFGVPPPPTT

421 SLVDTYRFVQ SVAITCQKDA APAENKDPYD KLKFWNVDLK EKFSLDLDQY PLGRKFLVQA

481 GLRRKPTIGP RKRSAPSATT SSKPAKRVRV RARK

SEQ ID NO: 4:
  1 MQMALWRPSD NTVYLPPPSV ARVVNTDDYV TRTSIFYHAG SSRLLTVGNP YFRVPAGGGN

61 KQDIPKVSAY QYRVFRVQLP DPNKFGLPDT SIYNPETQRL VWACAGVEIG RGQPLGVGLS

121 GHPFYNKLDD TESSHAATSN VSEDVRDNVS VDYKQTQLCI LGCAPAIGEH WAKGTACKSR

181 PLSQGDCPPL ELKNTVLEDG DMVDTGYGAM DFSTLQDTKC EVPLDICQSI CKYPDYLQMS

241 ADPYGDSMFF CLRREQLFAR HFWNRAGTMG DTVPQSLYIK GTGMRASPGS CVYSPSPSGS

301 IVTSDSQLFN KPYWLHKAQG HNNGVCWHNQ LFVTVVDTTR STNLTICAST QSPVPGQYDA

361 TKFKQYSRHV EEYDLQFIFQ LCTITLTADV MSYIHSMNSS ILEDWNFGVP PPPTTSLVDT

421 YRFVQSVAIT CQKDAAPAEN KDPYDKLKFW NVDLKEKFSL DLDQYPLGRK FLVQAGLRRK

481 PTIGPRKRSA PSATTSSKPA KRVRVRARK

SEQ ID NO: 5:
  1 MTVYLPPPSV ARVVNTDDYV TRTSIFYHAG SSRLLTVGNP YFRVPAGGGN KQDIPKVSAY

61 QYRVFRVQLP DPNKFGLPDT SIYNPETQRL VWACAGVEIG RGQPLGVGLS GHPFYNKLDD

121 TESSHAATSN VSEDVRDNVS VDYKQTQLCI LGCAPAIGEH WAKGTACKSR PLSQGDCPPL

181 ELKNTVLEDG DMVDTGYGAM DFSTLQDTKC EVPLDICQSI CKYPDYLQMS ADPYGDSMFF

241 CLRREQLFAR HFWNRAGTMG DTVPQSLYIK GTGMRASPGS CVYSPSPSGS IVTSDSQLFN

301 KPYWLHKAQGVHNNGVCWHNQ LFVTVVDTTR STNLTICAST QSPVPGQYDA TKFKQYSRHV

361 EEYDLQFIFQ LCTITLTADV MSYIHSMNSS ILEDWNFGVP PPPTTSLVDT YRFVQSVAIT

421 CQKDAAPAEN KDPYDKLKFW NVDLKEKFSL DLDQYPLGRK FLVQAGLRRK PTIGPRKRSA

481 PSATTSSKPA KRVRVRARK

SEQ ID NO: 6:
  1 ATGCGGCCT AGTGACAAT ACCGTATAT CTTCCACCT CCTTCTGTG CAAGAGTT

55 GTAAATACC GATGATTAC GTGACTCGC ACAAGCATA TTTTATCAT GCTGGCAGC

109 TCTAGATTA TTAACTGTT GGTAATCCA TATTTTAGG GTTCCTGCA GGTGGTGGC

163 AATAAGCAG GATATTCCT AAGGTTTCT GCATACCAA TATAGAGTA TTTAGGGTG

217 CAGTTACCT GACCCAAAT AAATTTGGT TTACCTGAT ACTAGTATT TATAATCCT

271 GAAACACAA CGTTTAGTG TGGGCCTGT GCTGGAGTG GAAATTGGC CGTGGTCAG

325 CCTTTAGGT GTTGGCCTT AGTGGGCAT CCATTTTAT AATAAATTA GATGACACT

379 GAAAGTTCC CATGCCGCC ACGTCTAAT GTTTCTGAG GACGTTAGG GACAATGTG
```

```
 433 TCTGTAGAT TATAAGCAG ACACAGTTA TGTATTTTG GGCTGTGCC CCTGCTATT

487 GGGGAACAC TGGGCTAAA GGCACTGCT TGTAAATCG CGTCCTTTA TCACAGGGC

541 GATTGCCCC CCTTTAGAA CTTAAAAAC ACAGTTTTG GAAGATGGT GATATGGTA

595 GATACTGGA TATGGTGCC ATGGACTTT AGTACATTG CAAGATACT AAATGTGAG

649 GTACCATTG GATATTTGT CAGTCTATT TGTAAATAT CCTGATTAT TTACAAATG

703 TCTGCAGAT CCTTATGGG GATTCCATG TTTTTTTGC TTACGGCGT GAGCAGCTT

757 TTTGCTAGG CATTTTTGG AATAGAGCA GGTACTATG GGTGACACT GTGCCTCAA

811 TCCTTATAT ATTAAAGGC ACAGGTATG CGTGCTTCA CCTGGCAGC TGTGTGTAT

865 TCTCCCTCT CCAAGTGGC TCTATTGTT ACCTCTGAC TCCCAGTTC TTTAATAAA

919 CCATATTGG TTACATAAG GCACAGGGT CATAACAAT GGTGTTTGC TGGCATAAT

973 CAATTATTT GTTACTGTG GTAGATACC ACTCGCAGT ACCAATTTA ACAATATGT

1027 GCTTCTACA CAGTCTCCT GTACCTGGG CAATATGAT GCTACCAAA TTTAAGCAG

1081 TATAGCAGA CATGTTGAG GAATATGAT TTGCAGTTT ATTTTTCAG TTGTGTACT

1135 ATTACTTTA ACTGCAGAT GTTATGTCC TATATTCAT AGTATGAAT AGCAGTATT

1189 TTAGAGGAT TGGAACTTT GGTGTTCCC CCCCCGCCA ACTACTAGT TTGGTGGAT

1243 ACATATCGT TTTGTACAA TCTGTTGCT ATTGCCTGT CAAAAGGAT GCTGCACCG

1297 GCTGAAAAT AAGGATCCC TATGATAAG TTAAAGTTT TGGAATGTG GATTTAAAG

1351 GAAAAGTTT TCTTTAGAC TTAGATCAA TATCCCCTT GGACGTAAA TTTTTGGTT

1405 CAGGCTGGA TTGCGTCGC AAGCCCACC ATAGGCCCT CGCAAACGT TCTGCTCCA

1459 TCTGCCACT ACGGCTTCT AAACCTGCC AAGCGTGTG CGTGTACGT GCCAGGAAC

1513 TAA
```

The description is further illustrated in combination with the Examples, wherein it is not limited to the Examples.

EXAMPLE 1

Expression of the Truncated HPV18 L1 Protein (SEQ ID NO.1)

Preparation of HPV18 L1 Gene Fragments as PCR Template

DNA extracted from the vaginal secretion of cervical cancer patients from Xiamen City in Fujian province was used as a template. Forward primer was 18H5430F: 5'-CCT CTT GGG ATG TGC CTG TAT AC-3' (SEQ ID NO:10) and reverse primer was 18H7190R: 5'-TAC AAA CAC AAC AAT AGA TGT ATA TA-3' (SEQ ID NO:11). PCR reaction was performed in a Biometra T3 PCR thermocycler using the following parameters:

| 94° C. denaturation | 5 min | |
| 94° C. denaturation | 50 sec | |
| 57° C. annealing | 50 sec | 25 cycles |
| 72° C. elongation | 2 min | |
| 72° C. elongation | 10 min | |

The specific amplification product, about 1.6 kb in length, was used as the template to produce the DNA fragments of the truncated HPV18 L1 in this invention.

Construction of Non-Fusion Expression Vector of Truncated HPV18L1 Gene

The DNA fragments (1.6 kb) produced in the previous step were used as the template for the next PCR reaction. The forward primer was 18N65F: 5'-CAT ATg CGG CCT AGT GAC AAT AC-3' (SEQ ID NO:12), at the 5' terminal of which the restriction endonuclease NdeI site was introduced. The sequence of NdeI site was CAT ATG, wherein ATG was the initiation codon in $E.\ coli$ system. The reverse primer was 18CR: 5'-CTC gAg TTA CTT CCT GGC ACG TAC ACG CAC A-3' (SEQ ID NO:13), at the 5' terminal of which the restriction endonuclease XhoI site was introduced. Amplification was performed in a Biometra T3 PCR thermocycler using the following parameters:

| 94° C. denaturation | 5 min | |
| 94° C. denaturation | 50 sec | |
| 57° C. annealing | 50 sec | 25 cycles |
| 72° C. polymerization | 2 min | |
| 72° C. polymerization | 10 min | |

The DNA fragments, about 1.5 kb in length, were obtained after amplification. The PCR products were linked to the pMD 18-T vector (Takara Biosciences). After digestion with NdeI/XhoI, it was identified that positive colonies, wherein the truncated HPV 18 L1 gene was inserted, were obtained, designated as pMD 18-T-HPV18N65C-L1.

The nucleotide sequence of interest, which was inserted into the plasmid pMD 18-T-HPV18N65C-L1, was determined as SEQ ID NO: 6 by Shanghai Boya Bio Co. through using M13+/−primers. SEQ ID NO:6 encodes the amino acid sequence set forth in SEQ ID NO:1 which corresponds to a HPV 18 L1 protein having 65 amino acids truncated at its N-terminal and no amino acid truncated at its C-terminal and was designated as HPV18N65C-L1.

The truncated HPV18N65C-L1 gene fragments were obtained by NdeI/XhoI digestion of plasmid pMD 18-T-HPV18N65C-L1. The fragments were linked to the prokaryotic expression vector pTrxFus digested with NdeI/XhoI (Invitrogen). Since the fusion protein was cleaved, the protein of interest was expressed immediately after initiating the expression of the amino acid Met, without other fusion proteins included. Colonies were screened with NdeI/XhoI digestion. Positive colonies containing the insert were labeled pTRX-HPV18N65C-L1. 1 µL plasmid pTRX-HPV18N65C-L1 (0.15 mg/ml) was used to transform 40 µL competent *E. coli* G1698 (Invitrogen) prepared by Calcium chloride method, and then were coated on solid CAA media (dissolving 6 g $Na_2HPO_4$, 3 g $KH_2PO_4$, 0.5 g NaCl, 1 g $NH_4Cl$, 20 g casein hydrolysate, 0.095 $MgCl_2$, 1.5 g agar powder, and 20 ml 50% glycerin in 900 ml deionized water, and was added) containing benzyl chloride (at a final concention of 100 mg/ml, the same as below). Plates were incubated at 30° C. for about 10-12 h until single colonies could be observed clearly. Single colonies from the plates were transferred to a tube containing 4 ml liquid IMC medium containing benzyl chloride. Cultures were incubated in a shaking incubator at 220 rpm for 10 h at 25° C., and then 1 ml bacterial solution was freeze-dried and stored at −70° C.

Expression of HPV18N65C-L1 in Large Scale

*E. coli* transformed with pTRX-HPV18N65C-L1 was taken from freeze-dried stain at −70° C., and diluted with a little sterile water, and then incubated in 50 mL IMC medium containing benzyl amine at 200 rpm and 30° C. for 8 h. Then, the cultures were transferred to ten flasks (5 ml cultures per flask), each of which contains 500 mL LB medium, and were incubated in a shaking incubator overnight at 200 rpm and 30° C. The cultures were the starter cultures.

A 50 L fermenter made by Shanghai Baoxing Biological Ltd was used in large-scale incubation. pH electrode was calibrated. 30 L LB medium was prepared and transferred into the fermenter, sterilized at 121° C. for 30 minutes. Dissolved oxygen electrode was calibrated, wherein the value was determined as 0 before introduction of air after sterilization and as 100% prior to inoculation after introduction of air while stirring at 100 rpm at the beginning.

Preparation of the feed: 30 g casein hydrolysates was dissolved in 100 mL deionized water to prepare a solution (30%), and 50 g glucose was dissolved in 100 ml deionized water to prepared a glucose solution (50%). The two mixtures were sterilized at 121° C. for 20 min.

On the second day, the starter cultures in the ten flasks (for a total of 5 L) were transferred to the fermenter. At 30° C. and pH 7.0, the dissolved $O_2$ was maintained at >40% by regulating agitation rate or air supply manually.

Flow Feed: 50% glucose and 30% casein hydrolysates were mixed at a 2:1 mass ratio.

Flow rates were as follows:
1 h: 5%
2 h: 10%
3 h: 20%
4 h: 40%
5 h to the end: 60%

When $OD_{600}$ reached about 10.0, the culture temperature was lowered to 25° C. and 4 g tryptophan was added to begin an induction culture of 4 h. Fermentation was halted when $OD_{600}$ reached about 40. The culture was then centrifuged to obtain strains (about 2.5 kg).

IMC Medium (1 liter):

| | |
|---|---|
| Na2HPO4 | 6 g |
| KH2PO4 | 3 g |
| NaCl | 0.5 g |
| NH4Cl | 1 g |
| Casein Hydrolysates | 20 g |
| MgCl2 | 0.095 g |

EXAMPLE 2

Preparation of HPV18N65C-L1 with a Purity of About 70%

1 g strains were re-suspended in 10 ml lysis buffer (20 mM tris buffer pH 7.2, 300 mM NaCl). Strains were disrupted by passing through a APV homogenizer (Invensys Group) for five times at a pressure of 600 bar. The homogenate was centrifuged at 30,000 g (13,500 rpm in JA-14 rotor) for 15 min. The supernatant was subjected to SDS-PAGE on a 10% gel. At this stage, the HPV18N65C-L1 had a purity of about 10%. The supernatant was dialyzed by a Centrasette 5 Tangential Flow Filter (Pall Co.) running at a pressure of 0.5 psi, a flow rate of 500 ml/min, and a tangential flow rate of 200 mL/min, wherein the retention molecular weight was 30 kDa, the dialysate was 10 mM phosphate buffer pH 6.0, and the dialysis volume was three times as large as the volume of supernatant. After thorough dialysis, the mixture was centrifuged at 12,000 g (9500 rpm in JA-10 rotor (Beckman J25 high speed centrifuge)) for 20 min, and the precipitation was collected. The precipitation was re-suspended in 10 mM phosphate buffer pH 7.0 containing 10 mM DTT and 300 mM NaCl, wherein the volume of the buffer was ¹/₁₀ times as large as the volume of the supernatant. The mixture was stirred for 30 min and centrifuged at 30,000 g (13,500 rpm in JA-14 rotor (Beckman J25 high speed centrifuge)) for 20 min. The supernatant passes through a 0.22 µm filter membrane. The sample was further subjected to cation exchange chromatography. 30 µL of 6× loading buffer was added to 150 µL of the filtered supernatant, and the result solution was mixed. After heating in a water bath at 80° C. for 10 min, the sample was subjected to SDS-PAGE on a 10% gel at 120V for 120 min. The electrophoretic bands were stained by Coomassie brilliant blue. The result was shown in FIG. 1. According to the analysis of SDS-PAGE, HPV18N65C-L1 protein was purified and enriched after the steps of precipitation and re-dissolution, with the purity increased from about 10% to about 70%.

EXAMPLE 3

Chromatography Purification of HPV18N65C-L1

Purification of HPV18N65C-L1 by Cation Exchange Chromatography
  Equipment: AKTA Explorer 100 preparative liquid chromatography system (GE Healthcare, i.e. the original Amershan Pharmacia Co.)
  Chromatographic media: SP Sepharose 4 Fast Flow
  Column Volume: 5.5 cm×20 cm
  Buffer: 20 mM phosphate buffer pH 7.0, 10 mM DTT
    20 mM phosphate buffer pH 7.0, 10 mM DTT, 2M NaCl
  Flow Rate: 25 mL/min
  Detector Wavelength: 280 nm Sample: 3 L 70% pure HPV18N65C-L1 solution
Elution protocol: eluting undesired proteins with 300 mM NaCl, eluting the protein of interest with 500 mM NaCl, collecting 500 mM NaCl elutate, and finally getting about 1000 mL purified HPV18N65C-L1 sample.
Purification of HPV18N65C-L1 by CHT-II Chromatography
Equipment: AKTA Explorer 100 preparative liquid chromatography system (GE Healthcare, i.e. the original Amershan Pharmacia Co.)
Chromatographic media: CHT-II (Bio-Rad)
Column Volume: 5.5 cm×20 cm
Buffer: 10 mM phosphate buffer pH 7.0, 10 mM DTT, 0.5M NaCl
Flow Rate: 20 mL/min
Detector Wavelength: 280 nm
Sample: 500 mM NaCl elutate from SP Sepharose 4 Fast Flow
Elution protocol: directly collecting the pass-through containing the protein of interest.

Figure 2:
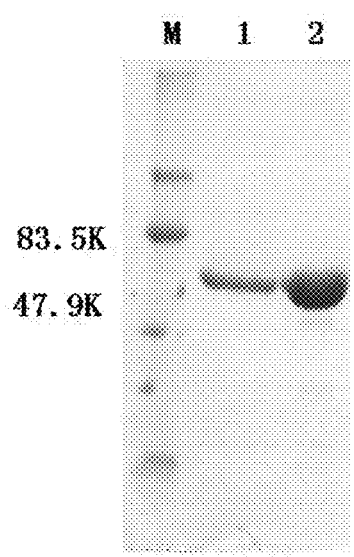
FIG. 2 shows the SDS-PAGE result of HPV18N65C-L1 that was obtained in step d) and was further purified according to step e). M: Molecular Weight Marker; Lane 1: HPV18N65C-L1 purified according to step e), 5 μL; Lane 2: HPV18N65C-L1 purified according to step e), 25 μL. The result shows that HPV18N65C-L1 purified according to step e) reached a purity of about 98%.

The pass-through, which contains HPV18N65C-L1, was collected and about 1100 mL purified HPV18N65C-L1 was obtained. 30 μL 6× loading buffer was added to 150 μL HPV18N65C-L1 sample purified according to the method of the Example, and then the result solution was mixed thoroughly. After heating the solution in a water bath at 80° C. for 10 min, a 10 uL sample was subjected to SDS-PAGE on a 10% gel at 120V for 120 min. The electrophoretic bands were stained by Coomassie brilliant blue. The result was shown in FIG. 2. The concentration of the protein of interest was about 0.8 mg/ml, and the purity was greater than 98% according to SDS-PAGE.

EXAMPLE 4

Assembly of HPV18N65C-L1 VLPs

Equipment: Centrasette 5 Tangential Flow Filter (Pall Co.), retention MW 30 kDa.
Sample: 1100 mL HPV18N65C-L1 obtained in Example 3
Sample Concentration: Sample was concentrated to 800 mL with the system tangential flow rate was adjusted to 50 mL/min
Sample renaturation: Sample Renaturation: Sample buffer was exchanged with 10 L renaturation buffer (20 mM PB pH 6.0, 2 mM $CaCl_2$, 2 mM $MgCl_2$, 0.5M NaCl) thoroughly. When running the Tangential Flow Filter, the pressure was 0.5 psi and the tangential flow rate was 10 mL/min. When exchange was finished, the sample buffer was replaced with storage buffer (20 L PBS: 20 mM PB pH 6.5, 0.5M NaCl). The exchange volume was 20 L. The running pressure was 0.5 psi and the tangential flow rate was 25 mL/min. When the liquid exchange was finished, the sample was aseptically filtrated with a Pall filter (0.20 μm). The filterated sample was incubated in an incubator at 37° C. overnight. The incubated HPV18N65C-L1 VLPs were stored at 4° C. for further use.

EXAMPLE 5

Determination of the Morphology and Immunogenicity of HPV18N65C-L1 VLPs

Figure 3:
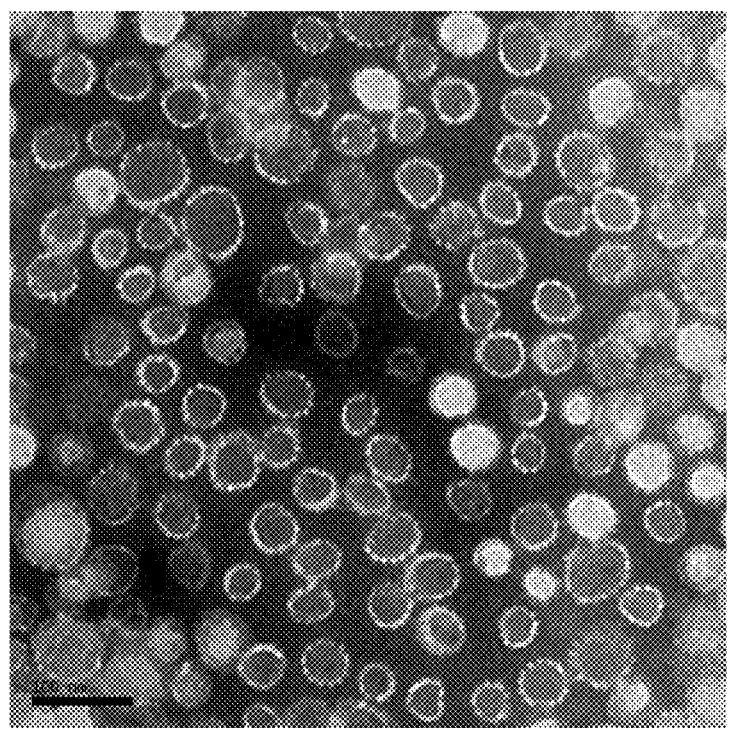
FIG. 3 shows the transmission electron microscopy (TEM) photograph of HPV18N65C-L1 VLPs obtained in step f), taken at 100,000× magnification, bar represents 0.1 μm. A great deal of VLPs in a radius of about 25 nm were observed in visual field, wherein the particle size was consistant with the theoretic size and the particles were homogenous.

Transmission Electron Microscopy (TEM) of HPV18N65C-L1 VLPs
The equipment was a JEOL 100 kV Transmission Electron Microscope (100,000× magnification). HPV18N65C-L1 VLPs were negatively stained with 2% phosphotungstic acid at pH 7.0, and fixed on a copper grid. Results were shown in FIG. 3. It could be seen that the VLPs obtained in Example 4 had a radius of approximately 25 nm, and were homogenous and in a hollow form.

Dynamic Light-Scattering Measurement of HPV18N65C-L1 VLPs

Figure 4:
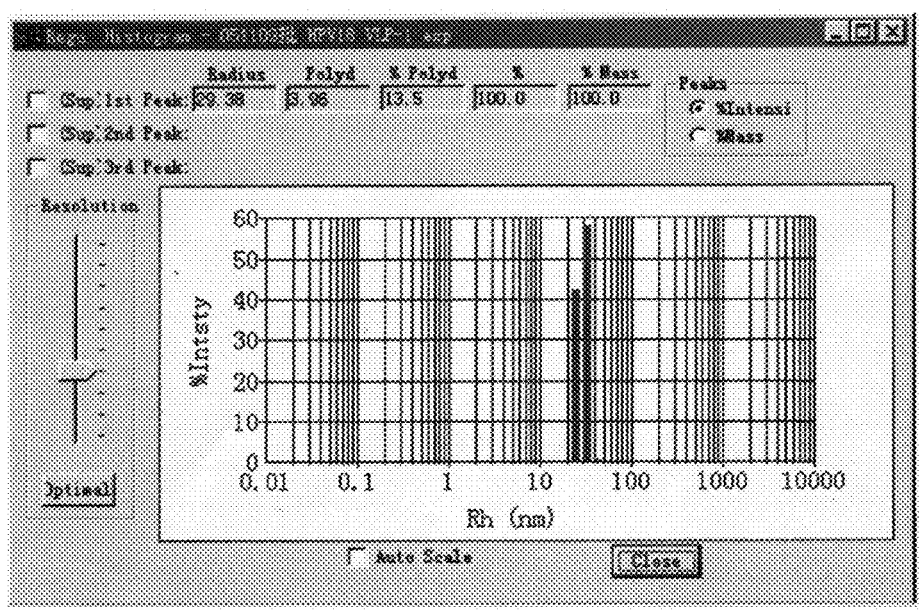
FIG. 4 shows the dynamic light-scattering measurement result of HPV18N65C-L1 VLPs obtained in step f). The result shows that HPV18N65C-L1 VLP had a hydrodynamic radius of 29.38 nm and a particle assembly rate of 100%.

DynaPro MS/X dynamic light-scattering instrument (including a temperature controller) (US Protein Solutions Co.) was used for light-scattering measurements. The regulation algorithm was used in the measurements. The sample was the one obtained in Example 4. The sample was passed through a 0.22 μm filter membrane prior to the measurement. Results were shown in FIG. 4. The result shows that HPV18N65C-L1 VLPs had a Hydrodynamic radius of 29.38 nm.

Establishment a Model of Pseudovirion Neutralization Assay for HPV18:

HPV can hardly be cultured in vitro, and the HPV host had a strong specificity. Thus, HPV can hardly be propagated in hosts other than human. That is, there was not an appropriate animal model for HPV. Therefore, in order to evaluate the immune productivity of HPV vaccine quickly, there was a need to establish a efficient model for in vitro neutralization assays.

In Vitro Infection Model of Pseudovirion: According to the characteristic that HPV VLP can package nucleic acids non-specifically, HPV pseudivirion was formed by expressing HPV L1 and L2 protein in cells, and by packaging viral DNA of episome or introducing reporter plasmids heterologously. Methods include expression systems based on recombinant viruses and cotransfection of multi-plasmids (see Yeager, M. D, Aste-Amezaga, M. et al (2000) Virology (278) 570-7).

The invention utilizes cotransfection of a multi-plasmid system. Some improvements were made as follows. An optimized calcium phosphate transfection method was established for the 293FT cell line, with a transfection efficiency of above 90%, which facilitate the production on a large scale. The resultant codon-optimized expression plasmid of HPV protein could express HPV L1 and L2 gene efficiently in mammalian cell lines, facilitating efficient assembly of pseudovirion.

1. Construction of HPV Pseudovirion:

P18L1h, p18L2h and pN31-EGFP (donated by Professor T. Schiller of NIH) contain genes for HPV18L1, HPV18L2, and GFP, respectively. These plasmids were purified using CsCl density gradient centrifugation as described in The Molecular Cloning Experiment Guide, (3rd edition). The purification procedure was as follows:

Plasmids were used to transform *E. coli* DH5α;

Single colonies were transferred into 500 mL LB culture medium and incubated in a shaking flask at 37° C. for 16 h;

Culture medium was centrifuged at 9,000 g for 5 min and the stains were collected;

The following substances were successively added to bacteria in each 1000 mL LB: 40 mL solution I (50 mM glucose, 25 mM Tris-Cl pH 8.0, 10 mM EDTA pH 8.0) and 2 ml 1 μg/μL RNase A), 40 mL solution II (0.2M NaOH, 1% SDS), and 48 mL solution III (60.0 mL 5M potassium acetate, 11.5 mL acetic acid, and 28.5 mL deionized water);

After placing on ice for 10 min, the mixture was centrifuged at 15,000 g for 20 min at 4° C.;

The supernatant was mixed with 0.6 volume of isopropyl alcohol, then was centrifuged again at 15,000 g for 30 min;

The supernatant was decanted into waste and the precipitation was washed with 70% ethanol;

The precipitation was dissolved in TE and the content of DNA was determined;

CsCl was dissolved in the solution of DNA (1 g DNA per 1.01 g CsCl), and then 100 μL 10 mg/mL EB solution was also dissolved in it;

The mixture was centrifuged using a Beckman NVT65 centrifuge at 62,000 rpm for 10 hr at 20° C.;

Closed circle DNA section was collected using an injector pinhead;

EB was extracted with equivalent volume of Isoamyl alcohol repeatedly for four times;

Three volumes of deionized water and eight volumes of dry ethanol were added to one volume of DNA solution, and then the mixture was centrifuged at 20000 g for 30 min at 4° C.;

The precipitation was collected and washed with 75% ethanol, and then dissolved in 1 mL TE;

The concentration of the DNA solution was determined, then the solution was stored in small packages at −20° C.

The purified p18L1h, p18L2h and pN31-EGFP 293FT co-transfect 293FT cells (Invitrogen) cultured on a 10 cm cell culture plate by calcium phosphate method. The calcium phosphate method was described as follows. 40 μg p18L1h, 40 μg p18L2h and 40 μg pN31-EGFP were separately added to the mixture of 1 mL HEPEs solution (125 μL 1M HEPES/50 mL deionized water, at pH7.3 and 4° C.) and 1 mL 0.5M $CaCl_2$ solution. After mixing, 2 mL 2× HeBS solution (0.28M NaCl (16.36 g), 0.05M HEPES (11.9 g), 1.5 mM $Na_2HPO_4$ (0.213 g), dissolved in 1000 mL deionized water, at pH 6.96 and −70° C.) was added dropwise. After standing at room temperature for 1 min, the mixture was added to the 10 cm cell culture plate where the 293FT cells were cultured. The original culture medium was replaced with 10 ml complete medium (Invitrogen Co.) 6 hours later. 48 hours after transfection, the medium was decanted and the cells were washed twice with PBS. Then, the cells were collected and counted. Every $10^8$ cells were suspended in 1 mL cytolytic solution (0.25% Brij58, 9.5 mM $MgCl_2$). After lysing, cell lysate was centrifugated at 5,000 g for 10 min and the supernatant was collected. The Pseudovirion solution was obtained after adding 5M NaCl to the supernatant to a final concentration of 850 mM, then was stored in small packages at −20° C.

293FT cells (Invitrogen) were spread on a 96-well cell culture plate ($1.5 \times 10^4$ cells/well). Neutralization assay was performed five hours later. Serum samples were serially diluted with 10% DMEM half-by-half. 50 μL diluted samples were separately mixed with 50 μL Pseudovirion solutions diluted with 10% DMEM (moi=0.1). After incubating at 4° C. for 1 h, the mixture was added to the 96-well cell culture plate spread with 293FT cells. The mixture was then incubated for 72 h at 37° C. Neutralization titers of samples were estimated by observing fluorescence. Infection percentage of cells in each well was checked by flow cytometry (EPICS XL, American Beckman Coulter Co.). The exact titers of monoclonal antibodies or polyclonal antibodies were calculated. Infection percentage was the percentage of cells in the positive region minus the uninfected cells in the positive region.

Infection control percentage=(1−infection percentage of sample cell/infection percentage of negative cell)×100%

Neutralization titer was defined as the highest dilution multiple by which the infection control percentage was just above 50%. Monoclonal and polyclonal antibodies were considered as having neutralizing capacity if their infection control percentage was above 50% after 50 times dilutions.

Immune Protectivity of Animals Inoculated with HPV18 VLPs

50% Effective Dose ($ED_{50}$) Assay in Mouse: HPV18N65C-L1 VLPs produced in Example 4 were adsorbed on aluminum hydroxide adjuvant, and then were diluted with vaccine diluents to four different concentrations at a ratio of 1:3 (i.e. 0.1 μg/mL, 0.033 μg/mL, 0.011 μg/mL and 0.004 μg/mL). In each experimental group, ten BALB/c mice were inoculated with 1 mL of the above vaccine by intraperitoneal injection. Serum was collected at the forth and fifth weeks after injection, and HPV neutralizing antibodies were evaluated by the EIA and pseudovirion neutralization assays. After the last serum collection, the mice were sacrificed. The control group includes ten BALB/c mice.

Cutoff value for EIA was average negative value plus 0.16 (if average negative value was below 0.05, 0.05 was used in the calculation). Before inoculation, all BALB/c mice show negative in the HPV neutralizing antibody assays, results were shown in Table 1.

TABLE 1

$ED_{50}$ result of HPV18N65C-L1 VLPs in BALB/c Mice by EIA Assay

| Concentration μg/mL | Number of mouse | 4 weeks | | 5 weeks | |
|---|---|---|---|---|---|
| | | Positive number | Positive rate (%) | Positive number | Positive rate (%) |
| 0.100 | 10 | 10 | 100.00 | 10 | 100.00 |
| 0.033 | 10 | 10 | 100.00 | 10 | 100.00 |
| 0.011 | 10 | 6 | 66.67 | 6 | 66.67 |
| 0.004 | 10 | 2 | 14.29 | 2 | 14.29 |

ED50 was calculated according to the Reed-Muench method. After inoculation, blood was collected for detecting $ED_{50}$ at the forth and fifth week. HPV18N65C-L1 VLPs had a $ED_{50}$ of 0.008 μg at the forth week and 0.008 μg at the fifth week. Therefore, immunization in these dosages could induce high levels of neutralizing antibodies. The efficacy of these dosages was far less than that of 0.1 μg.

Results in the pseudovirion neutralization assay could only be accepted when more than 20% of the cells in the negative control group and none of the cells in the positive control group fluoresce. It was considered as a positive result when less than 50% of the cells in the negative control group fluoresce. Results were shown in Table 2.

TABLE 2

$ED_{50}$ result of HPV18N65C-L1 VLPs in BALB/c Mice in Pseudovirion Neutralization Assay

| Concentration μg/mL | Number of mice | 4 weeks | | 5 weeks | |
|---|---|---|---|---|---|
| | | Positive number | Positive rate (%) | Positive number | Positive rate (%) |
| 0.100 | 10 | 10 | 100 | 10 | 100 |
| 0.033 | 10 | 10 | 100 | 9 | 92 |
| 0.011 | 10 | 1 | 10 | 3 | 27 |
| 0.004 | 10 | 0 | 0 | 0 | 0 |

ED50 was calculated according to the Reed-Muench method. After inoculation, blood was collected for detecting $ED_{50}$ at the forth and fifth week. HPV18N65C-L1 VLPs had a $ED_{50}$ of 0.018 μg at the forth week and 0.016 μg at the fifth week. Therefore, immunization in these dosages could induce high levels of neutralizing antibodies. The efficacy of these dosages was far less than that of 0.1 μg.

Female rabbits (general level), 6-8 weeks old, were purchased from the Disease Prevention and Control Center of Guangxi province, where they were raised. HPV18N65C-L1 VLPs prepared in Example 4, were mixed with equal amount of complete Freund's Adjuvant for the first immunization.

For the booster, HPV18N65C-L1 VLPs were mixed with incomplete Freund's Adjuvant. Rabbits were immunized via muscle injection, with 100 μg per rabbit for the first immunization, and with 50 μg per rabbit for the booster separately at week 4, 10. After immunization, external vein blood was collected every week, and serum was separated and stored for detection.

Female goats (general level), 6-8 weeks old, were purchased from the Disease Prevention and Control Center of Guangxi province, where they were raised. HPV18N65C-L1 VLPs as prepared in Example 4, were mixed with equal amount of complete Freund's adjuvant for the first immunization. For the booster, HPV18N65C-L1 VLPs were mixed with incomplete Freund's adjuvant. Goats were immunized via muscle injection, with 1 mg per goat for the first immunization, and with 0.5 mg per goat for the booster separately at weeks 4, 10 and 18. After immunization, external vein blood was collected, and serum was separated and stored for detection.

Figure 5:
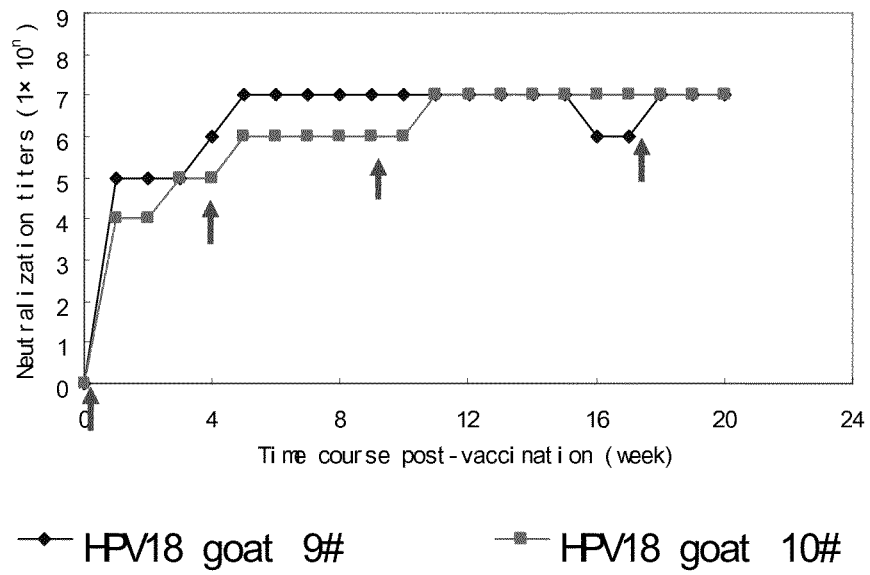
FIG. 5 shows titers of neutralizing antibodies in serum at different stages after inoculation of goat with HPV18N65C-L1 VLPs. Vaccination times are indicated with arrows. The titer of neutralizing antibodies increased rapidly a week after the first vaccination, and reached a peak level of $10^7$ after a booster.
Figure 6:
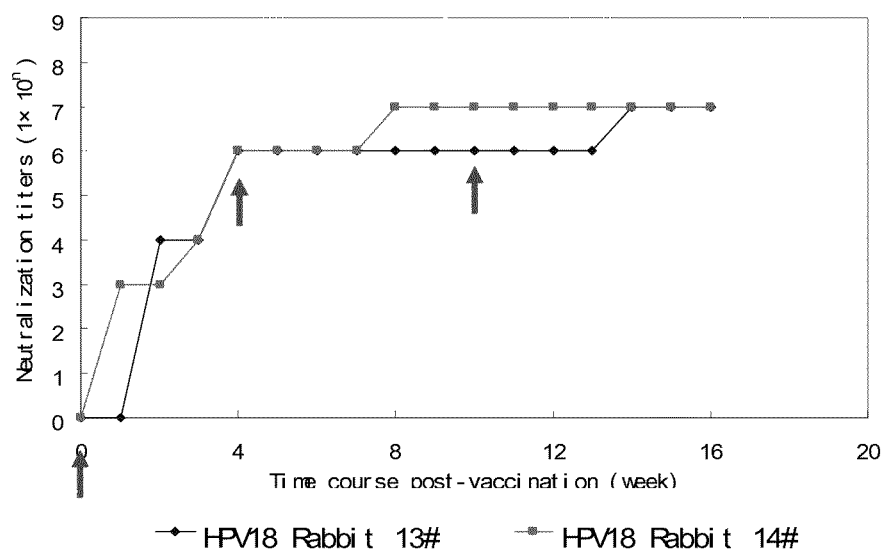
FIG. 6 shows titers of neutralizing antibodies in serum at different stages a week after inoculation of rabbit with HPV18N65C-L1 VLPs. Vaccination times are indicated with arrows. The titer of neutralizing antibodies increased rapidly after the first vaccination, and reached a peak level of $10^6$ after a booster.

Neutralization titers of the anti-serums were evaluated using a pseudovirion-based neutralization cell model assay. As shown in FIGS. 5 and 6, the vaccine produced by mixing HPV18N65C-L1 VLPs prepared in Example 4 with aluminum hydroxide or aluminum phosphate adjuvants available commercially or self-prepared in addition to Freund's adjuvants, had good immunogenicity, could induce neutralizing antibodies with a high titer in animals, and could be used as an effective vaccine for the prevention of HPV infection.

Immune Response of Rhesus Monkeys Inoculated With HPV16/18 Bivalent Vaccine

Female rhesus monkeys (General level), 2 years old, were purchased from the Disease Prevention and Control Center of Guangxi Province, where they were raised. HPV18N65C-L1 prepared in Example 4 were adsorbed on aluminum hydroxide adjuvants, and HPV16N30C-L1 VLPs prepared according to the method similar to that of Example 4 were also adsorbed on aluminum hydroxide adjuvants. Then, the two were mixed at a ratio of 2:1 by weight to produce a bivalent HPV16/18 vaccine. Each dose (0.5 ml) contained 40 μg HPV16N30C-L1 VLPs, 20 μg HPV18N65C-L1 VLPs and 0.6 mg aluminum hydroxide. The Rhesus monkeys were separately administrated with 5 μg, 10 μg and 20 μg HPV 18 by injection in deltoid of the upper-limb (on triplicate). All the candidate animals show that the total IgG antibodies and neutralizing antibodies against HPV 18 were negative before immunization. Vaccine was administered at 0 and 4 weeks. The animals were raised for 9 weeks, and blood was collected everyweek. Blood samples were stored at 37° C. for 1.5 h, and then centrifuged at 10,000 rpm for 5 min. Serum was collected to assay titers of total IgG and neutralizing antibodies against HPV16 and HPV18. Similar assay methods were used for the two types of antibodies.

Figure 7:
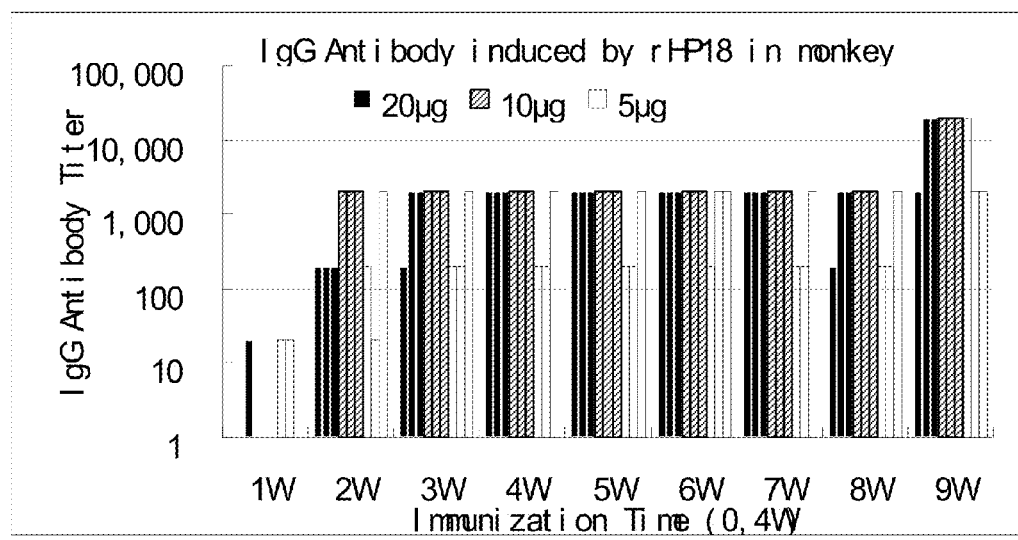
FIG. 7 shows the titers of total immunoglobulin G (IgG) antibody against HPV 18 in serum at different times after inoculation of rhesus monkey with HPV16/18 bivalent vaccine obtained in Example 5. Vaccine was administered at 0 and 4 weeks. The total IgG antibody titer increased rapidly after the first vaccination, reaching 20,000 times of the original one.
Figure 8:
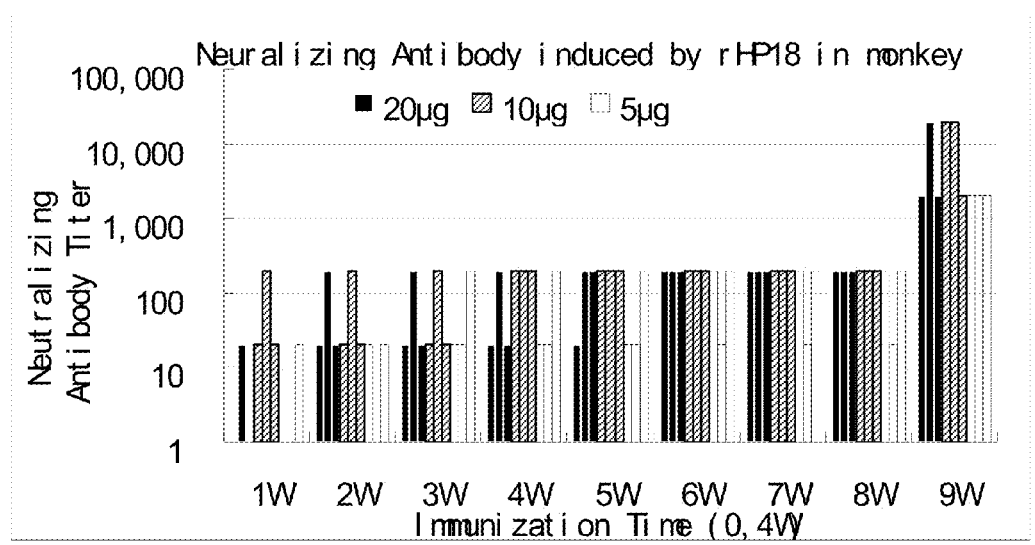
FIG. 8 shows the titers of neutralizing antibodies against HPV 18 in serum at different times after inoculation of rhesus monkey with HPV16/18 bivalent vaccine obtained in Example 5. Vaccine was administered at 0 and 4 weeks. The total IgG antibody titer increased rapidly after the first vaccination, reaching 20,000 times of the original one.
Figure 9:
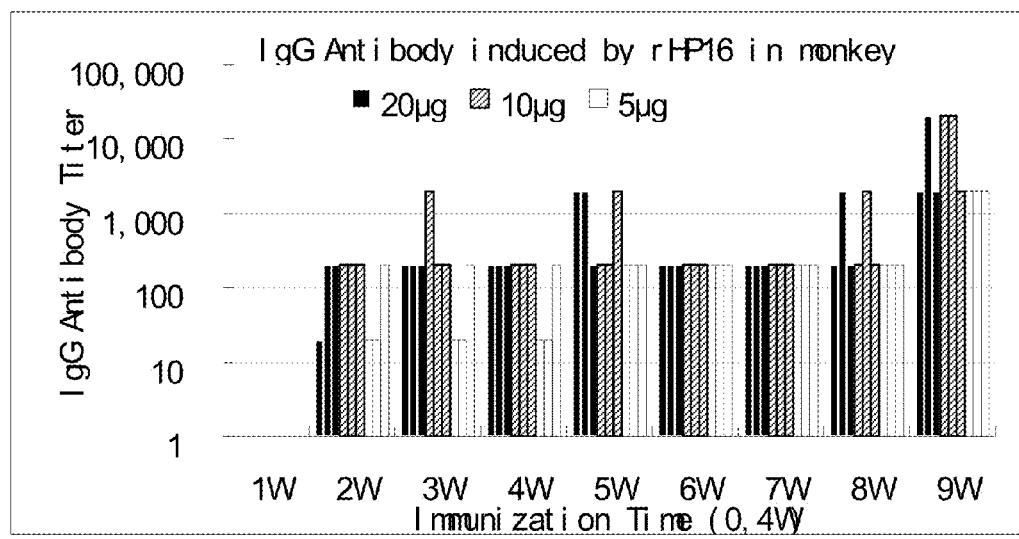
FIG. 9 shows the titers of total immunoglobulin G (IgG) antibody against HPV 16 in serum at different times after inoculation of rhesus monkey with HPV16/18 bivalent vaccine obtained in Example 5. Vaccine was administered at 0 and 4 weeks. The total IgG antibody titer increased rapidly after the first vaccination, reaching 20,000 times of the original one.
Figure 10:
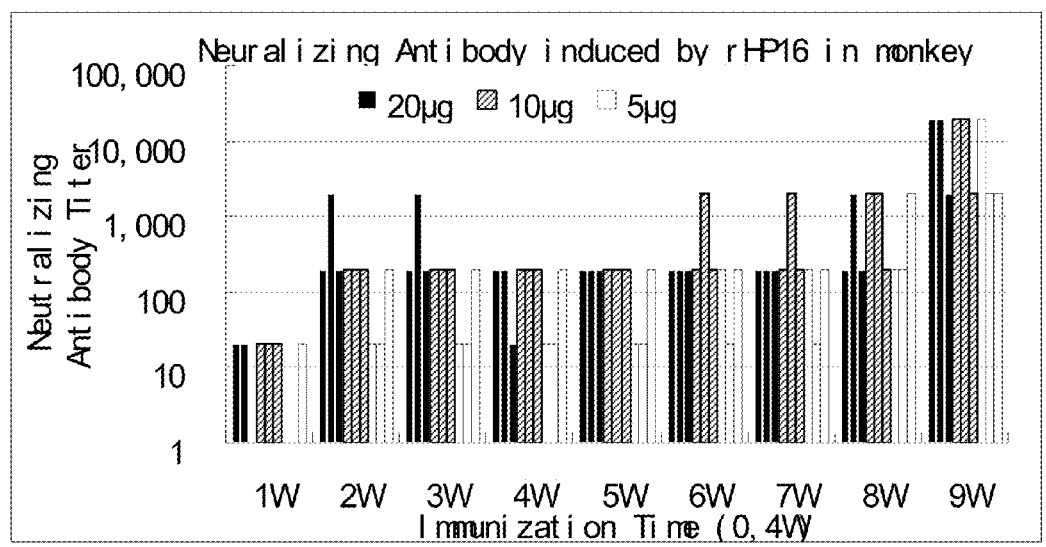
FIG. 10 shows the titers of neutralizing antibodies against HPV 16 in serum at different times after inoculation of rhesus monkey with HPV16/18 bivalent vaccine obtained in Example 5. Vaccine was administered at 0 and 4 weeks. The total IgG antibody titer increased rapidly after the first vaccination, reaching 20,000 times of the original one.

As shown in FIG. 7 and FIG. 8, HPV18N65C-L1 VLPs according to the invention could induce high titers of total IgG and neutralizing antibodies, exceeding 20,000 at week 9 after the first immunization. HPV18N65C-L1 VLPs had good immunogenicity and could be used as an effective vaccine for the prevention of HPV18 infection. Also, HPV16N30C-L1 VLPs of the Bivalent Vaccine could induce high titers of total IgG and neutralizing antibodies against HPV16, exceeding 20,000 at week 9 after the first immunization, as shown in FIG. 9 and FIG. 10. HPV16N30C-L1 VLPs had good immunogenicity and could also be used as an effective vaccine for the prevention of HPV18 infection.

The Amino Acid Sequence of HPV16N30C-L1 is showed in SEQ ID NO 7 as follows.

```
Met Leu Pro Ser Glu Ala Thr Val Tyr Leu Pro Pro Val Pro Val Ser
1               5                   10                  15

Lys Val Val Ser Thr Asp Glu Tyr Val Ala Arg Thr Asn Ile Tyr Tyr
                20                  25                  30

His Ala Gly Thr Ser Arg Leu Leu Ala Val Gly His Pro Tyr Phe Pro
            35                  40                  45

Ile Lys Lys Pro Asn Asn Asn Lys Ile Leu Val Pro Lys Val Ser Gly
        50              55                  60

Leu Gln Tyr Arg Val Phe Arg Ile His Leu Pro Asp Pro Asn Lys Phe
65                  70              75                      80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
                100                 105                 110

Gly Ile Ser Gly His Pro Leu Leu Asn Lys Leu Asp Asp Thr Glu Asn
            115                 120                 125

Ala Ser Ala Tyr Ala Ala Asn Ala Gly Val Asp Asn Arg Glu Cys Ile
        130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
                180                 185                 190

Gln Asp Gly Asp Met Val Asp Thr Gly Phe Gly Ala Met Asp Phe Thr
            195                 200                 205
```

-continued

```
Thr Leu Gln Ala Asn Lys Ser Glu Val Pro Leu Asp Ile Cys Thr Ser
    210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Ala Val Gly Asp Asn Val Pro Asp Asp Leu
            260                 265                 270

Tyr Ile Lys Gly Ser Gly Ser Thr Ala Asn Leu Ala Ser Ser Asn Tyr
        275                 280                 285

Phe Pro Thr Pro Ser Gly Ser Met Val Thr Ser Asp Ala Gln Ile Phe
    290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
                325                 330                 335

Thr Asn Met Ser Leu Cys Ala Ala Ile Ser Thr Ser Glu Thr Thr Tyr
            340                 345                 350

Lys Asn Thr Asn Phe Lys Glu Tyr Leu Arg His Gly Glu Glu Tyr Asp
        355                 360                 365

Leu Gln Phe Ile Phe Gln Leu Cys Lys Ile Thr Leu Thr Ala Asp Ile
    370                 375                 380

Met Thr Tyr Ile His Ser Met Asn Ser Thr Ile Leu Glu Asp Trp Asn
385                 390                 395                 400

Phe Gly Leu Gln Pro Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
            420                 425                 430

Pro Lys Glu Asp Pro Leu Lys Lys Tyr Thr Phe Trp Glu Val Asn Leu
        435                 440                 445

Lys Glu Lys Phe Ser Ala Asp Leu Asp Gln Phe Pro Leu Gly Arg Lys
    450                 455                 460

Phe Leu Leu Gln Ala Gly Leu Glu Ala Lys Pro Lys Phe Thr Leu Gly
465                 470                 475                 480

Lys Arg Lys Ala Thr Pro Thr Thr Ser Ser Thr Ser Thr Thr Ala Lys
                485                 490                 495

Arg Lys Lys Arg Lys Leu
                500
```

Immune Protectivity of Mice Inoculated with HPV6/11/16/18 Quadrivalent Vaccine

Four SPF BALB/c mice, 4-5 weeks old, were used. HPV6N5C-L1, HPV11N4C-L1, HPV16N30C-L1 and HPV18N65C-L1 VLPs, prepared according to the method similar to that of Example 4, were mixed at a ratio of 1:2:2:1 (by weight), wherein the final concentrations of them were 40 μg/mL, 80 μg/mL, 80 μg/mL and 40 μg/mL, respectively. The vaccine was mixed with an equal amount of complete Freund's adjuvant for the first immunization, and was mixed with an equal amount of incomplete Freund's adjuvant for the booster.

Mice were immunized by muscle injection. The amount for the first immunization was 10 μg HPV6N5C-L1, 10 μg HPV18N65C-L1, 20 μg HPV11N4C-L1, and 20 μg HPV16N30C-L1 per mouse. The booster was administered every two weeks. The amount for the booster was 20 μg HPV6N5C-L1, 20 μg HPV18N65C-L1, 40 μg HPV11N4C-L1, and 40 μg HPV16N30C-L1 per mouse.

After immunization, external vein blood was collected every week and serum was separated. The titers of neutralizing antibodies against HPV6, HPV11, HPV16 and HPV18 in immunized mice were separately determined according to the method of Example 5.

Figure 11:
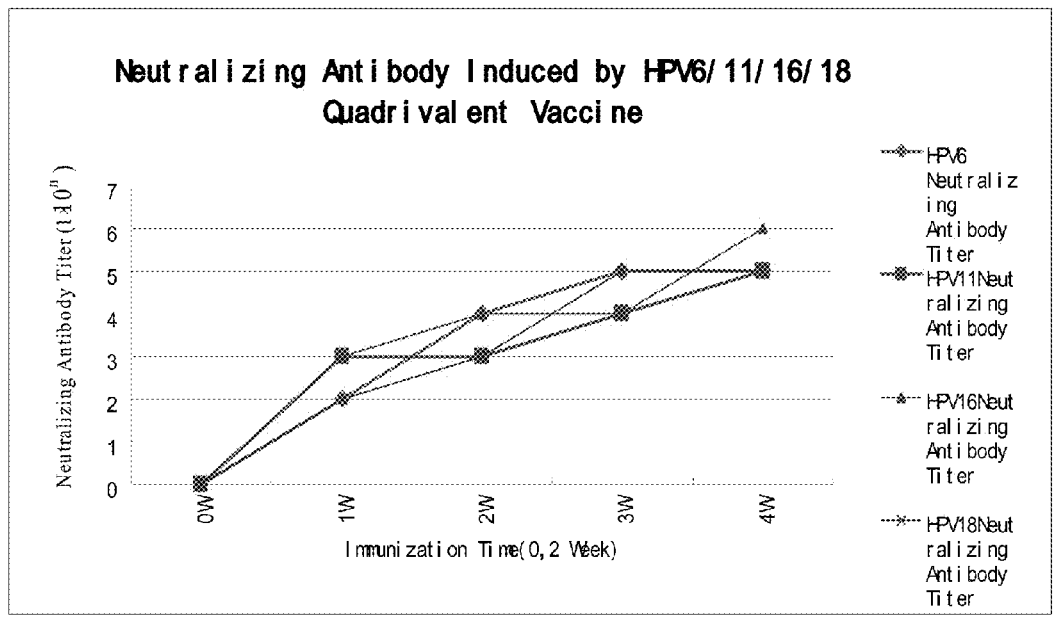
FIG. 11 shows the changes of titers of neutralizing antibodies against HPV6, HPV11, HPV16 and HPV18 after inoculation of mouse with HPV6/11/16/18 quadrivalent vaccine obtained in Example 5. Vaccine was administered at 0 and 2 weeks. The titers of neutralizing antibodies against HPV6, HPV11, HPV16 and HPV18 increased rapidly after the first vaccination, reaching $10^5$-$10^6$ after a booster.

Results were shown in FIG. 11, indicating that HPV6/11/16/18 quadrivalent vaccine, prepared by blending HPV6N5C-L1, HPV11N4C-L1, HPV16N30C-L1 and HPV18N65C-L1 VLPs as prepared in Examples 1-4, had good immunogenicity, could induce netralizing antibodies with a high titer against HPV 6, HPV 11, HPV 16, and HPV 18 in animals, and could be used as a effective vaccine for the prevention of HPV6/HPV11/HPV16/HPV18 infection (in addition to the Freund's adjuvants used in the experiments, the vaccine could be prepared by blending the four HPV6N5C-L1, HPV11N4C-L1, HPV16N30C-L1 and HPV18N65C-L1 VLPs with aluminum hydroxide or aluminum phosphate adjuvants available commercially or self-prepared).

The Amino Acid Sequence of HPV6N5C-L1 is showed in SEQ ID NO 8 as follows.

Met Asp Ser Thr Val Tyr Val Pro Pro Asn Pro Val Ser Lys Val
1               5                   10                  15

Val Ala Thr Asp Ala Tyr Val Thr Arg Thr Asn Ile Phe Tyr His Ala
            20                  25                  30

Ser Ser Ser Arg Leu Leu Ala Val Gly His Pro Tyr Phe Ser Ile Lys
            35                  40                  45

Arg Ala Asn Lys Thr Val Val Pro Lys Val Ser Gly Tyr Gln Tyr Arg
        50                  55                  60

Val Phe Lys Val Val Leu Pro Asp Pro Asn Lys Phe Ala Leu Pro Asp
65                  70                  75                  80

Ser Ser Leu Phe Asp Pro Thr Thr Gln Arg Leu Val Trp Ala Cys Thr
            85                  90                  95

Gly Leu Glu Val Gly Arg Gly Gln Pro Leu Gly Val Gly Val Ser Gly
            100                 105                 110

His Pro Phe Leu Asn Lys Tyr Asp Asp Val Glu Asn Ser Gly Ser Gly
            115                 120                 125

Gly Asn Pro Gly Gln Asp Asn Arg Val Asn Val Gly Met Asp Tyr Lys
        130                 135                 140

Gln Thr Gln Leu Cys Met Val Gly Cys Ala Pro Pro Leu Gly Glu His
145                 150                 155                 160

Trp Gly Lys Gly Lys Gln Cys Thr Asn Thr Pro Val Gln Ala Gly Asp
            165                 170                 175

Cys Pro Pro Leu Glu Leu Ile Thr Ser Val Ile Gln Asp Gly Asp Met
            180                 185                 190

Val Asp Thr Gly Phe Gly Ala Met Asn Phe Ala Asp Leu Gln Thr Asn
            195                 200                 205

Lys Ser Asp Val Pro Ile Asp Ile Cys Gly Thr Thr Cys Lys Tyr Pro
        210                 215                 220

Asp Tyr Leu Gln Met Ala Ala Asp Pro Tyr Gly Asp Arg Leu Phe Phe
225                 230                 235                 240

Phe Leu Arg Lys Glu Gln Met Phe Ala Arg His Phe Phe Asn Arg Ala
            245                 250                 255

Gly Glu Val Gly Glu Pro Val Pro Asp Thr Leu Ile Ile Lys Gly Ser
            260                 265                 270

Gly Asn Arg Thr Ser Val Gly Ser Ser Ile Tyr Val Asn Thr Pro Ser
            275                 280                 285

Gly Ser Leu Val Ser Ser Glu Ala Gln Leu Phe Asn Lys Pro Tyr Trp
            290                 295                 300

Leu Gln Lys Ala Gln Gly His Asn Asn Gly Ile Cys Trp Gly Asn Gln
305                 310                 315                 320

Leu Phe Val Thr Val Asp Thr Thr Arg Ser Thr Asn Met Thr Leu
            325                 330                 335

Cys Ala Ser Val Thr Thr Ser Ser Thr Tyr Thr Asn Ser Asp Tyr Lys
            340                 345                 350

Glu Tyr Met Arg His Val Glu Glu Tyr Asp Leu Gln Phe Ile Phe Gln
            355                 360                 365

Leu Cys Ser Ile Thr Leu Ser Ala Glu Val Val Ala Tyr Ile His Thr
            370                 375                 380

Met Asn Pro Ser Val Leu Glu Asp Trp Asn Phe Gly Leu Ser Pro Pro
385                 390                 395                 400

Pro Asn Gly Thr Leu Glu Asp Thr Tyr Arg Tyr Val Gln Ser Gln Ala
            405                 410                 415

```
Ile Thr Cys Gln Lys Pro Thr Pro Glu Lys Gln Lys Pro Asp Pro Tyr
            420                 425                 430

Lys Asn Leu Ser Phe Trp Glu Val Asn Leu Lys Glu Lys Phe Ser Ser
        435                 440                 445

Glu Leu Asp Gln Tyr Pro Leu Gly Arg Lys Phe Leu Leu Gln Ser Gly
    450                 455                 460

Tyr Arg Gly Arg Ser Ser Ile Arg Thr Gly Val Lys Arg Pro Ala Val
465                 470                 475                 480

Ser Lys Ala Ser Ala Ala Pro Lys Arg Lys Arg Ala Lys Thr Lys Arg
            485                 490                 495
```

The Amino Acid Sequence of HPV11N4C-L1 is showed in SEQ ID NO 9:

```
Met Ser Asp Ser Thr Val Tyr Val Pro Pro Asn Pro Val Ser Lys
1               5                   10                  15

Val Val Ala Thr Asp Ala Tyr Val Lys Arg Thr Asn Ile Phe Tyr His
            20                  25                  30

Ala Ser Ser Arg Leu Leu Ala Val Gly His Pro Tyr Tyr Ser Ile
        35                  40                  45

Lys Lys Val Asn Lys Thr Val Val Pro Lys Val Ser Gly Tyr Gln Tyr
    50                  55                  60

Arg Val Phe Lys Val Val Leu Pro Asp Pro Asn Lys Phe Ala Leu Pro
65                  70                  75                  80

Asp Ser Ser Leu Phe Asp Pro Thr Thr Gln Arg Leu Val Trp Ala Cys
                85                  90                  95

Thr Gly Leu Glu Val Gly Arg Gly Gln Pro Leu Gly Val Gly Val Ser
            100                 105                 110

Gly His Pro Leu Leu Asn Lys Tyr Asp Asp Val Glu Asn Ser Gly Gly
        115                 120                 125

Tyr Gly Gly Asn Pro Gly Gln Asp Asn Arg Val Asn Val Gly Met Asp
130                 135                 140

Tyr Lys Gln Thr Gln Leu Cys Met Val Gly Cys Ala Pro Pro Leu Gly
145                 150                 155                 160

Glu His Trp Gly Lys Gly Thr Gln Cys Ser Asn Thr Ser Val Gln Asn
                165                 170                 175

Gly Asp Cys Pro Pro Leu Glu Leu Ile Thr Ser Val Ile Gln Asp Gly
            180                 185                 190

Asp Met Val Asp Thr Gly Phe Gly Ala Met Asn Phe Ala Asp Leu Gln
        195                 200                 205

Thr Asn Lys Ser Asp Val Pro Leu Asp Ile Cys Gly Thr Val Cys Lys
    210                 215                 220

Tyr Pro Asp Tyr Leu Gln Met Ala Ala Asp Pro Tyr Gly Asp Arg Leu
225                 230                 235                 240

Phe Phe Tyr Leu Arg Lys Glu Gln Met Phe Ala Arg His Phe Phe Asn
                245                 250                 255

Arg Ala Gly Thr Val Gly Glu Pro Val Pro Asp Asp Leu Leu Val Lys
            260                 265                 270

Gly Gly Asn Asn Arg Ser Ser Val Ala Ser Ser Ile Tyr Val His Thr
        275                 280                 285

Pro Ser Gly Ser Leu Val Ser Ser Glu Ala Gln Leu Phe Asn Lys Pro
    290                 295                 300

Tyr Trp Leu Gln Lys Ala Gln Gly His Asn Asn Gly Ile Cys Trp Gly
305                 310                 315                 320
```

```
                                    -continued
Asn His Leu Phe Val Thr Val Val Asp Thr Thr Arg Ser Thr Asn Met
                325                 330                 335

Thr Leu Cys Ala Ser Val Ser Lys Ser Ala Thr Tyr Thr Asn Ser Asp
            340                 345                 350

Tyr Lys Glu Tyr Met Arg His Val Glu Glu Phe Asp Leu Gln Phe Ile
        355                 360                 365

Phe Gln Leu Cys Ser Ile Thr Leu Ser Ala Glu Val Met Ala Tyr Ile
    370                 375                 380

His Thr Met Asn Pro Ser Val Leu Glu Asp Trp Asn Phe Gly Leu Ser
385                 390                 395                 400

Pro Pro Pro Asn Gly Thr Leu Glu Asp Thr Tyr Arg Tyr Val Gln Ser
10                  405                 410                 415

Gln Ala Ile Thr Cys Gln Lys Pro Thr Pro Glu Lys Glu Lys Gln Asp
            420                 425                 430

Pro Tyr Lys Asp Met Ser Phe Trp Glu Val Asn Leu Lys Glu Lys Phe
        435                 440                 445

Ser Ser Glu Leu Asp Gln Phe Pro Leu Gly Arg Lys Phe Leu Leu Gln
    450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
                485                 490                 495

Lys Lys
```

The Amino Acid Sequence of HPV16N30C-L1 VLP is shown in SEQ ID NO:7, as described above.

The experimental results show that the vaccine that was formed by HPV18N65C-L1 VLPs prepared in Example 4 (in addition to the Freund's adjuvants used in the experiments, aluminum hydroxide or aluminum phosphate adjuvants available commercially or self-prepared could also be used) had good immunogenicity could induce neutralizing antibodies with a high titer in animals, and could be an effective vaccine useful for the prevention of HPV18 infection.

EXAMPLE 6

The truncated HPV18L1 proteins set forth in SEQ ID NOs: 2, 3, 4 and 5 were prepared according to the techniques used in examples 1-5. All these truncated proteins could be assembled into VLPs.

The invention claimed is:

1. An isolated N-terminally truncated HPV18 L1 protein, wherein the amino acid sequence of the truncated HPV18 L1 protein consists of the amino acid sequence of SEQ ID NO:1, 2, 3, 4, or 5.

2. A polynucleotide encoding an N-terminally truncated HPV 18 L1 protein consisting of the amino acid sequence of SEQ ID NO:1, 2, 3, 4, or 5.

3. A vector comprising the polynucleotide of claim 2.

4. A cell comprising the vector of claim 3.

5. A composition comprising the protein of claim 1.

6. A HPV18 virus-like particle (VLP) comprising the protein of claim 1.

7. A vaccine for the prevention of cervical cancer, comprising:
the HPV 18 VLP of claim 6 and a carrier or excipient.

8. The vaccine of claim 7, wherein the HPV18 VLP comprises a protein consisting of the amino acid sequence of SEQ ID NO:1.

9. The vaccine of claim 7, further comprising at least one HPV VLP selected from the group consisting of VLPs of HPV types 6, 11, 16, 31, 33, 45, 52, and 58.

10. The vaccine of claim 9, wherein the HPV16 VLP comprises a protein comprising the amino acid sequence of SEQ ID NO:7.

11. The vaccine of claim 9, wherein the HPV6 VLP comprises a protein comprising the amino acid sequence of SEQ ID NO:8.

12. The vaccine of claim 9, wherein the HPV11 VLP comprises a protein comprising the amino acid sequence of SEQ ID NO:9.

13. A method for producing the HPV18 L1 protein, the method comprising:
   a) expressing a gene encoding the HPV18 L1 protein of claim 1 in an *E. coli* expression system;
   b) disrupting the *E. coli*, which has expressed the protein, in a solution with a salt concentration of 100 mM to 600 mM, and isolating a supernatant;
   c) decreasing the salt concentration of the supernatant to 0 mM to 100 mM, by using water or a low salt solution to produce a precipitate;
   d) collecting the precipitate; and
   e) redissolving the precipitate in a solution with a salt concentration of 150 mM to 2500 mM, adding a reductant to it, and then isolating the resultant solution, wherein the resultant solution contains the HPV18 L1 protein of claim 1 with a purity of at least 50%.

14. A method for providing a VLP of a HPV18 L1 protein, the method comprising:
   a) expressing the polynucleotide of claim 2 in an *E. coli* expression system;
   b) disrupting the *E. coli*, which has expressed the HPV18 L1 protein, in a solution with a salt concentration of 100 mM to 600 mM, and isolating a supernatant;
   c) decreasing the salt concentration of the supernatant to 0 mM to 100 mM, by using water or a low salt solution to produce a precipitate;
   d) collecting the precipitate;
   e) redissolving the precipitate in a solution at a salt concentration of 150 mM to 2500 mM, adding a reductant to it, and then isolating the resultant solution, wherein the resultant solution contains the HPV18 L1 protein with a purity of at least 50%;
   f) further purifying the HPV18 L1 protein by chromatography; and
   g) removing the reductant from the HPV18 L1 protein.

15. A method for producing a vaccine for the prevention of cervical cancer, comprising mixing the VLP of claim 6, and optionally, one or more VLPs selected from the group consisting of VLPs of HPV types 6, 11, 16, 31, 33, 45, 52, and 58, with carriers or excipients for vaccines.

16. A method for preventing cervical cancer, the method comprising administering a vaccine comprising a preventively effective amount of the HPV18 L1 protein of claim 1, a VLP comprising the protein of claim 1, or a vaccine comprising a HPV18 VLP comprising the protein of claim 2 to an individual in need of it.

* * * * *

SEQUENCE LISTING

```
<160> NUMBER OF SEQ ID NOS: 13

<210> SEQ ID NO 1
<211> LENGTH: 504
<212> TYPE: PRT
<213> ORGANISM: Artificial Sequence
<220> FEATURE:
<223> OTHER INFORMATION: Synthesized in the laboratory

<400> SEQUENCE: 1

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
            35                  40                  45

Val Pro Ala Gly Gly Gly Asn Lys Gln Asp Ile Pro Lys Val Ser Ala
        50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95
```

```
Trp Ala Cys Ala Gly Val Glu Ile Gly Arg Gly Gln Pro Leu Gly Val
            100                 105                 110
Gly Leu Ser Gly His Pro Phe Tyr Asn Lys Leu Asp Asp Thr Glu Ser
        115                 120                 125
Ser His Ala Ala Thr Ser Asn Val Ser Glu Asp Val Arg Asp Asn Val
    130                 135                 140
Ser Val Asp Tyr Lys Gln Thr Gln Leu Cys Ile Leu Gly Cys Ala Pro
145                 150                 155                 160
Ala Ile Gly Glu His Trp Ala Lys Gly Thr Ala Cys Lys Ser Arg Pro
                165                 170                 175
Leu Ser Gln Gly Asp Cys Pro Pro Leu Glu Leu Lys Asn Thr Val Leu
            180                 185                 190
Glu Asp Gly Asp Met Val Asp Thr Gly Tyr Gly Ala Met Asp Phe Ser
        195                 200                 205
Thr Leu Gln Asp Thr Lys Cys Glu Val Pro Leu Asp Ile Cys Gln Ser
    210                 215                 220
Ile Cys Lys Tyr Pro Asp Tyr Leu Gln Met Ser Ala Asp Pro Tyr Gly
225                 230                 235                 240
Asp Ser Met Phe Phe Cys Leu Arg Arg Glu Gln Leu Phe Ala Arg His
                245                 250                 255
Phe Trp Asn Arg Ala Gly Thr Met Gly Asp Thr Val Pro Gln Ser Leu
            260                 265                 270
Tyr Ile Lys Gly Thr Gly Met Arg Ala Ser Pro Gly Ser Cys Val Tyr
        275                 280                 285
Ser Pro Ser Pro Ser Gly Ser Ile Val Thr Ser Asp Ser Gln Leu Phe
    290                 295                 300
Asn Lys Pro Tyr Trp Leu His Lys Ala Gln Gly His Asn Asn Gly Val
305                 310                 315                 320
Cys Trp His Asn Gln Leu Phe Val Thr Val Asp Thr Thr Arg Ser
                325                 330                 335
Thr Asn Leu Thr Ile Cys Ala Ser Thr Gln Ser Pro Val Pro Gly Gln
            340                 345                 350
Tyr Asp Ala Thr Lys Phe Lys Gln Tyr Ser Arg His Val Glu Glu Tyr
        355                 360                 365
Asp Leu Gln Phe Ile Phe Gln Leu Cys Thr Ile Thr Leu Thr Ala Asp
    370                 375                 380
Val Met Ser Tyr Ile His Ser Met Asn Ser Ser Ile Leu Glu Asp Trp
385                 390                 395                 400
Asn Phe Gly Val Pro Pro Pro Thr Thr Ser Leu Val Asp Thr Tyr
                405                 410                 415
Arg Phe Val Gln Ser Val Ala Ile Ala Cys Gln Lys Asp Ala Ala Pro
            420                 425                 430
Ala Glu Asn Lys Asp Pro Tyr Asp Lys Leu Lys Phe Trp Asn Val Asp
        435                 440                 445
Leu Lys Glu Lys Phe Ser Leu Asp Leu Asp Gln Tyr Pro Leu Gly Arg
    450                 455                 460
Lys Phe Leu Val Gln Ala Gly Leu Arg Arg Lys Pro Thr Ile Gly Pro
465                 470                 475                 480
Arg Lys Arg Ser Ala Pro Ser Ala Thr Thr Ala Ser Lys Pro Ala Lys
                485                 490                 495
Arg Val Arg Val Arg Ala Arg Lys
                500
```

-continued

<210> SEQ ID NO 2
<211> LENGTH: 519
<212> TYPE: PRT
<213> ORGANISM: Artificial Sequence
<220> FEATURE:
<223> OTHER INFORMATION: Synthesized in the laboratory

<400> SEQUENCE: 2

```
Met Arg Asn Val Asn Val Phe Pro Ile Phe Leu Gln Met Ala Leu Trp
1               5                   10                  15

Arg Pro Ser Asp Asn Thr Val Tyr Leu Pro Pro Ser Val Ala Arg
            20                  25                  30

Val Val Asn Thr Asp Asp Tyr Val Thr Arg Thr Ser Ile Phe Tyr His
            35                  40                  45

Ala Gly Ser Ser Arg Leu Leu Thr Val Gly Asn Pro Tyr Phe Arg Val
        50                  55                  60

Pro Ala Gly Gly Gly Asn Lys Gln Asp Ile Pro Lys Val Ser Ala Tyr
65                  70                  75                  80

Gln Tyr Arg Val Phe Arg Val Gln Leu Pro Asp Pro Asn Lys Phe Gly
                85                  90                  95

Leu Pro Asp Thr Ser Ile Tyr Asn Pro Glu Thr Gln Arg Leu Val Trp
            100                 105                 110

Ala Cys Ala Gly Val Glu Ile Gly Arg Gly Gln Pro Leu Gly Val Gly
        115                 120                 125

Leu Ser Gly His Pro Phe Tyr Asn Lys Leu Asp Asp Thr Glu Ser Ser
    130                 135                 140

His Ala Ala Thr Ser Asn Val Ser Glu Asp Val Arg Asp Asn Val Ser
145                 150                 155                 160

Val Asp Tyr Lys Gln Thr Gln Leu Cys Ile Leu Gly Cys Ala Pro Ala
                165                 170                 175

Ile Gly Glu His Trp Ala Lys Gly Thr Ala Cys Lys Ser Arg Pro Leu
            180                 185                 190

Ser Gln Gly Asp Cys Pro Pro Leu Glu Leu Lys Asn Thr Val Leu Glu
        195                 200                 205

Asp Gly Asp Met Val Asp Thr Gly Tyr Gly Ala Met Asp Phe Ser Thr
    210                 215                 220

Leu Gln Asp Thr Lys Cys Glu Val Pro Leu Asp Ile Cys Gln Ser Ile
225                 230                 235                 240

Cys Lys Tyr Pro Asp Tyr Leu Gln Met Ser Ala Asp Pro Tyr Gly Asp
                245                 250                 255

Ser Met Phe Phe Cys Leu Arg Arg Glu Gln Leu Phe Ala Arg His Phe
            260                 265                 270

Trp Asn Arg Ala Gly Thr Met Gly Asp Thr Val Pro Gln Ser Leu Tyr
        275                 280                 285

Ile Lys Gly Thr Gly Met Arg Ala Ser Pro Gly Ser Cys Val Tyr Ser
    290                 295                 300

Pro Ser Pro Ser Gly Ser Ile Val Thr Ser Asp Ser Gln Leu Phe Asn
305                 310                 315                 320

Lys Pro Tyr Trp Leu His Lys Ala Gln Gly His Asn Asn Gly Val Cys
                325                 330                 335

Trp His Asn Gln Leu Phe Val Thr Val Val Asp Thr Thr Arg Ser Thr
            340                 345                 350

Asn Leu Thr Ile Cys Ala Ser Thr Gln Ser Pro Val Pro Gly Gln Tyr
        355                 360                 365

Asp Ala Thr Lys Phe Lys Gln Tyr Ser Arg His Val Glu Glu Tyr Asp
```

```
                    370                 375                 380
Leu Gln Phe Ile Phe Gln Leu Cys Thr Ile Thr Leu Thr Ala Asp Val
385                 390                 395                 400

Met Ser Tyr Ile His Ser Met Asn Ser Ser Ile Leu Glu Asp Trp Asn
                    405                 410                 415

Phe Gly Val Pro Pro Pro Thr Thr Ser Leu Val Asp Thr Tyr Arg
                420                 425                 430

Phe Val Gln Ser Val Ala Ile Thr Cys Gln Lys Asp Ala Ala Pro Ala
            435                 440                 445

Glu Asn Lys Asp Pro Tyr Asp Lys Leu Lys Phe Trp Asn Val Asp Leu
        450                 455                 460

Lys Glu Lys Phe Ser Leu Asp Leu Asp Gln Tyr Pro Leu Gly Arg Lys
465                 470                 475                 480

Phe Leu Val Gln Ala Gly Leu Arg Arg Lys Pro Thr Ile Gly Pro Arg
                485                 490                 495

Lys Arg Ser Ala Pro Ser Ala Thr Thr Ser Ser Lys Pro Ala Lys Arg
            500                 505                 510

Val Arg Val Arg Ala Arg Lys
            515

<210> SEQ ID NO 3
<211> LENGTH: 514
<212> TYPE: PRT
<213> ORGANISM: Artificial Sequence
<220> FEATURE:
<223> OTHER INFORMATION: Synthesized in the laboratory

<400> SEQUENCE: 3

Met Phe Pro Ile Phe Leu Gln Met Ala Leu Trp Arg Pro Ser Asp Asn
1               5                   10                  15

Thr Val Tyr Leu Pro Pro Ser Val Ala Arg Val Val Asn Thr Asp
            20                  25                  30

Asp Tyr Val Thr Arg Thr Ser Ile Phe Tyr His Ala Gly Ser Ser Arg
            35                  40                  45

Leu Leu Thr Val Gly Asn Pro Tyr Phe Arg Val Pro Ala Gly Gly Gly
50                  55                  60

Asn Lys Gln Asp Ile Pro Lys Val Ser Ala Tyr Gln Tyr Arg Val Phe
65                  70                  75                  80

Arg Val Gln Leu Pro Asp Pro Asn Lys Phe Gly Leu Pro Asp Thr Ser
                85                  90                  95

Ile Tyr Asn Pro Glu Thr Gln Arg Leu Val Trp Ala Cys Ala Gly Val
            100                 105                 110

Glu Ile Gly Arg Gly Gln Pro Leu Gly Val Gly Leu Ser Gly His Pro
        115                 120                 125

Phe Tyr Asn Lys Leu Asp Asp Thr Glu Ser Ser His Ala Ala Thr Ser
130                 135                 140

Asn Val Ser Glu Asp Val Arg Asp Asn Val Ser Val Asp Tyr Lys Gln
145                 150                 155                 160

Thr Gln Leu Cys Ile Leu Gly Cys Ala Pro Ala Ile Gly Glu His Trp
                165                 170                 175

Ala Lys Gly Thr Ala Cys Lys Ser Arg Pro Leu Ser Gln Gly Asp Cys
            180                 185                 190

Pro Pro Leu Glu Leu Lys Asn Thr Val Leu Glu Asp Gly Asp Met Val
        195                 200                 205

Asp Thr Gly Tyr Gly Ala Met Asp Phe Ser Thr Leu Gln Asp Thr Lys
```

```
                    210                 215                 220
Cys Glu Val Pro Leu Asp Ile Cys Gln Ser Ile Cys Lys Tyr Pro Asp
225                 230                 235                 240

Tyr Leu Gln Met Ser Ala Asp Pro Tyr Gly Asp Ser Met Phe Phe Cys
                245                 250                 255

Leu Arg Arg Glu Gln Leu Phe Ala Arg His Phe Trp Asn Arg Ala Gly
            260                 265                 270

Thr Met Gly Asp Thr Val Pro Gln Ser Leu Tyr Ile Lys Gly Thr Gly
        275                 280                 285

Met Arg Ala Ser Pro Gly Ser Cys Val Tyr Ser Pro Ser Pro Ser Gly
    290                 295                 300

Ser Ile Val Thr Ser Asp Ser Gln Leu Phe Asn Lys Pro Tyr Trp Leu
305                 310                 315                 320

His Lys Ala Gln Gly His Asn Asn Gly Val Cys Trp His Asn Gln Leu
                325                 330                 335

Phe Val Thr Val Val Asp Thr Thr Arg Ser Thr Asn Leu Thr Ile Cys
                340                 345                 350

Ala Ser Thr Gln Ser Pro Val Pro Gly Gln Tyr Asp Ala Thr Lys Phe
            355                 360                 365

Lys Gln Tyr Ser Arg His Val Glu Glu Tyr Asp Leu Gln Phe Ile Phe
        370                 375                 380

Gln Leu Cys Thr Ile Thr Leu Thr Ala Asp Val Met Ser Tyr Ile His
385                 390                 395                 400

Ser Met Asn Ser Ser Ile Leu Glu Asp Trp Asn Phe Gly Val Pro Pro
                405                 410                 415

Pro Pro Thr Thr Ser Leu Val Asp Thr Tyr Arg Phe Val Gln Ser Val
                420                 425                 430

Ala Ile Thr Cys Gln Lys Asp Ala Ala Pro Ala Glu Asn Lys Asp Pro
            435                 440                 445

Tyr Asp Lys Leu Lys Phe Trp Asn Val Asp Leu Lys Glu Lys Phe Ser
        450                 455                 460

Leu Asp Leu Asp Gln Tyr Pro Leu Gly Arg Lys Phe Leu Val Gln Ala
465                 470                 475                 480

Gly Leu Arg Arg Lys Pro Thr Ile Gly Pro Arg Lys Arg Ser Ala Pro
                485                 490                 495

Ser Ala Thr Thr Ser Ser Lys Pro Ala Lys Arg Val Arg Val Arg Ala
                500                 505                 510

Arg Lys

<210> SEQ ID NO 4
<211> LENGTH: 509
<212> TYPE: PRT
<213> ORGANISM: Artificial Sequence
<220> FEATURE:
<223> OTHER INFORMATION: Synthesized in the laboratory

<400> SEQUENCE: 4

Met Gln Met Ala Leu Trp Arg Pro Ser Asp Asn Thr Val Tyr Leu Pro
1               5                   10                  15

Pro Pro Ser Val Ala Arg Val Val Asn Thr Asp Asp Tyr Val Thr Arg
                20                  25                  30

Thr Ser Ile Phe Tyr His Ala Gly Ser Ser Arg Leu Leu Thr Val Gly
            35                  40                  45

Asn Pro Tyr Phe Arg Val Pro Ala Gly Gly Gly Asn Lys Gln Asp Ile
        50                  55                  60
```

```
Pro Lys Val Ser Ala Tyr Gln Tyr Arg Val Phe Arg Val Gln Leu Pro
 65                  70                  75                  80

Asp Pro Asn Lys Phe Gly Leu Pro Asp Thr Ser Ile Tyr Asn Pro Glu
             85                  90                  95

Thr Gln Arg Leu Val Trp Ala Cys Ala Gly Val Glu Ile Gly Arg Gly
            100                 105                 110

Gln Pro Leu Gly Val Gly Leu Ser Gly His Pro Phe Tyr Asn Lys Leu
            115                 120                 125

Asp Asp Thr Glu Ser Ser His Ala Ala Thr Ser Asn Val Ser Glu Asp
130                 135                 140

Val Arg Asp Asn Val Ser Val Asp Tyr Lys Gln Thr Gln Leu Cys Ile
145                 150                 155                 160

Leu Gly Cys Ala Pro Ala Ile Gly Glu His Trp Ala Lys Gly Thr Ala
                165                 170                 175

Cys Lys Ser Arg Pro Leu Ser Gln Gly Asp Cys Pro Pro Leu Glu Leu
            180                 185                 190

Lys Asn Thr Val Leu Glu Asp Gly Asp Met Val Asp Thr Gly Tyr Gly
            195                 200                 205

Ala Met Asp Phe Ser Thr Leu Gln Asp Thr Lys Cys Glu Val Pro Leu
210                 215                 220

Asp Ile Cys Gln Ser Ile Cys Lys Tyr Pro Asp Tyr Leu Gln Met Ser
225                 230                 235                 240

Ala Asp Pro Tyr Gly Asp Ser Met Phe Phe Cys Leu Arg Arg Glu Gln
                245                 250                 255

Leu Phe Ala Arg His Phe Trp Asn Arg Ala Gly Thr Met Gly Asp Thr
            260                 265                 270

Val Pro Gln Ser Leu Tyr Ile Lys Gly Thr Gly Met Arg Ala Ser Pro
            275                 280                 285

Gly Ser Cys Val Tyr Ser Pro Ser Pro Ser Gly Ser Ile Val Thr Ser
290                 295                 300

Asp Ser Gln Leu Phe Asn Lys Pro Tyr Trp Leu His Lys Ala Gln Gly
305                 310                 315                 320

His Asn Asn Gly Val Cys Trp His Asn Gln Leu Phe Val Thr Val Val
                325                 330                 335

Asp Thr Thr Arg Ser Thr Asn Leu Thr Ile Cys Ala Ser Thr Gln Ser
            340                 345                 350

Pro Val Pro Gly Gln Tyr Asp Ala Thr Lys Phe Lys Gln Tyr Ser Arg
            355                 360                 365

His Val Glu Glu Tyr Asp Leu Gln Phe Ile Phe Gln Leu Cys Thr Ile
            370                 375                 380

Thr Leu Thr Ala Asp Val Met Ser Tyr Ile His Ser Met Asn Ser Ser
385                 390                 395                 400

Ile Leu Glu Asp Trp Asn Phe Gly Val Pro Pro Pro Thr Thr Ser
                405                 410                 415

Leu Val Asp Thr Tyr Arg Phe Val Gln Ser Val Ala Ile Thr Cys Gln
            420                 425                 430

Lys Asp Ala Ala Pro Ala Glu Asn Lys Asp Pro Tyr Asp Lys Leu Lys
            435                 440                 445

Phe Trp Asn Val Asp Leu Lys Glu Lys Phe Ser Leu Asp Leu Asp Gln
            450                 455                 460

Tyr Pro Leu Gly Arg Lys Phe Leu Val Gln Ala Gly Leu Arg Arg Lys
465                 470                 475                 480
```

```
Pro Thr Ile Gly Pro Arg Lys Arg Ser Ala Pro Ser Ala Thr Thr Ser
                485                 490                 495

Ser Lys Pro Ala Lys Arg Val Arg Val Arg Ala Arg Lys
            500                 505
```

<210> SEQ ID NO 5
<211> LENGTH: 499
<212> TYPE: PRT
<213> ORGANISM: Artificial Sequence
<220> FEATURE:
<223> OTHER INFORMATION: Synthesized in the laboratory

<400> SEQUENCE: 5

```
Met Thr Val Tyr Leu Pro Pro Ser Val Ala Arg Val Val Asn Thr
1               5                   10                  15

Asp Asp Tyr Val Thr Arg Thr Ser Ile Phe Tyr His Ala Gly Ser Ser
                20                  25                  30

Arg Leu Leu Thr Val Gly Asn Pro Tyr Phe Arg Val Pro Ala Gly Gly
                35                  40                  45

Gly Asn Lys Gln Asp Ile Pro Lys Val Ser Ala Tyr Gln Tyr Arg Val
            50                  55                  60

Phe Arg Val Gln Leu Pro Asp Pro Asn Lys Phe Gly Leu Pro Asp Thr
65                  70                  75                  80

Ser Ile Tyr Asn Pro Glu Thr Gln Arg Leu Val Trp Ala Cys Ala Gly
                85                  90                  95

Val Glu Ile Gly Arg Gly Gln Pro Leu Gly Val Gly Leu Ser Gly His
                100                 105                 110

Pro Phe Tyr Asn Lys Leu Asp Asp Thr Glu Ser Ser His Ala Ala Thr
                115                 120                 125

Ser Asn Val Ser Glu Asp Val Arg Asp Asn Val Ser Val Asp Tyr Lys
            130                 135                 140

Gln Thr Gln Leu Cys Ile Leu Gly Cys Ala Pro Ala Ile Gly Glu His
145                 150                 155                 160

Trp Ala Lys Gly Thr Ala Cys Lys Ser Arg Pro Leu Ser Gln Gly Asp
                165                 170                 175

Cys Pro Pro Leu Glu Leu Lys Asn Thr Val Leu Glu Asp Gly Asp Met
                180                 185                 190

Val Asp Thr Gly Tyr Gly Ala Met Asp Phe Ser Thr Leu Gln Asp Thr
                195                 200                 205

Lys Cys Glu Val Pro Leu Asp Ile Cys Gln Ser Ile Cys Lys Tyr Pro
            210                 215                 220

Asp Tyr Leu Gln Met Ser Ala Asp Pro Tyr Gly Asp Ser Met Phe Phe
225                 230                 235                 240

Cys Leu Arg Arg Glu Gln Leu Phe Ala Arg His Phe Trp Asn Arg Ala
                245                 250                 255

Gly Thr Met Gly Asp Thr Val Pro Gln Ser Leu Tyr Ile Lys Gly Thr
                260                 265                 270

Gly Met Arg Ala Ser Pro Gly Ser Cys Val Tyr Ser Pro Ser Pro Ser
            275                 280                 285

Gly Ser Ile Val Thr Ser Asp Ser Gln Leu Phe Asn Lys Pro Tyr Trp
            290                 295                 300

Leu His Lys Ala Gln Gly His Asn Asn Gly Val Cys Trp His Asn Gln
305                 310                 315                 320

Leu Phe Val Thr Val Val Asp Thr Thr Arg Ser Thr Asn Leu Thr Ile
                325                 330                 335
```

Cys Ala Ser Thr Gln Ser Pro Val Pro Gly Gln Tyr Asp Ala Thr Lys
                340                 345                 350

Phe Lys Gln Tyr Ser Arg His Val Glu Glu Tyr Asp Leu Gln Phe Ile
            355                 360                 365

Phe Gln Leu Cys Thr Ile Thr Leu Thr Ala Asp Val Met Ser Tyr Ile
        370                 375                 380

His Ser Met Asn Ser Ser Ile Leu Glu Asp Trp Asn Phe Gly Val Pro
385                 390                 395                 400

Pro Pro Pro Thr Thr Ser Leu Val Asp Thr Tyr Arg Phe Val Gln Ser
                405                 410                 415

Val Ala Ile Thr Cys Gln Lys Asp Ala Ala Pro Ala Glu Asn Lys Asp
            420                 425                 430

Pro Tyr Asp Lys Leu Lys Phe Trp Asn Val Asp Leu Lys Glu Lys Phe
        435                 440                 445

Ser Leu Asp Leu Asp Gln Tyr Pro Leu Gly Arg Lys Phe Leu Val Gln
    450                 455                 460

Ala Gly Leu Arg Arg Lys Pro Thr Ile Gly Pro Arg Lys Arg Ser Ala
465                 470                 475                 480

Pro Ser Ala Thr Thr Ser Ser Lys Pro Ala Lys Arg Val Arg Val Arg
                485                 490                 495

Ala Arg Lys

<210> SEQ ID NO 6
<211> LENGTH: 1515
<212> TYPE: DNA
<213> ORGANISM: Artificial Sequence
<220> FEATURE:
<223> OTHER INFORMATION: Synthesized in the laboratory

<400> SEQUENCE: 6

```
atgcggccta gtgacaatac cgtatatctt ccacctcctt ctgtggcaag agttgtaaat      60
accgatgatt acgtgactcg cacaagcata ttttatcatg ctggcagctc tagattatta    120
actgttggta atccatattt tagggttcct gcaggtggtg gcaataagca ggatattcct    180
aaggtttctg cataccaata tagagtattt agggtgcagt acctgacccc aaataaattt    240
ggtttacctg atactagtat ttataatcct gaaacacaac gtttagtgtg gcctgtgct    300 ggagtggaaa ttggccgtgg tcagccttta ggtgttggcc ttagtgggca tccattttat    360
aataaattag atgacactga agttcccat gccgccacgt ctaatgtttc tgaggacgtt    420
agggacaatg tgtctgtaga ttataagcag acacagttat gtattttggg ctgtgcccct    480
gctattgggg aacactgggc taaaggcact gcttgtaaat cgcgtccttt atcacagggc    540
gattgccccc ctttagaact aaaaacaca gttttggaag atggtgatat ggtagatact    600
ggatatggtg ccatggactt tagtacattg caagatacta atgtgaggt accattggat    660 atttgtcagt ctatttgtaa atatcctgat tatttacaaa tgtctgcaga tccttatggg    720
gattccatgt ttttttgctt acggcgtgag cagcttttg ctaggcattt ttggaataga    780
gcaggtacta tgggtgacac tgtgcctcaa tccttatata ttaaaggcac aggtatgcgt    840
gcttcacctg gcagctgtgt gtattctccc tctccaagtg gctctattgt tacctctgac    900
tcccagttgt ttaataaacc atattggtta cataaggcac agggtcataa caatggtgtt    960
tgctggcata tcaattatt tgttactgtg gtagatacca ctcgcagtac caattaaca   1020 atatgtgctt ctacacagtc tcctgtacct gggcaatatg atgctaccaa atttaagcag   1080
tatagcagac atgttgagga atatgatttg cagtttattt ttcagttgtg tactattact   1140
```

```
ttaactgcag atgttatgtc ctatattcat agtatgaata gcagtatttt agaggattgg   1200
aactttggtg ttcccccccc gccaactact agtttggtgg atacatatcg ttttgtacaa   1260
tctgttgcta ttgcctgtca aaaggatgct gcaccggctg aaaataagga tccctatgat   1320 aagtaaagt tttggaatgt ggatttaaag gaaaagtttt ctttagactt agatcaatat    1380
ccccttggac gtaaatttt ggttcaggct ggattgcgtc gcaagcccac cataggccct    1440
cgcaaacgtt ctgctccatc tgccactacg gcttctaaac ctgccaagcg tgtgcgtgta   1500
cgtgccagga agtaa                                                    1515
```

<210> SEQ ID NO 7
<211> LENGTH: 502
<212> TYPE: PRT
<213> ORGANISM: Artificial Sequence
<220> FEATURE:
<223> OTHER INFORMATION: Synthesized in the laboratory

<400> SEQUENCE: 7

```
Met Leu Pro Ser Glu Ala Thr Val Tyr Leu Pro Val Pro Val Ser
1               5                   10                  15

Lys Val Val Ser Thr Asp Glu Tyr Val Ala Arg Thr Asn Ile Tyr Tyr
            20                  25                  30

His Ala Gly Thr Ser Arg Leu Leu Ala Val Gly His Pro Tyr Phe Pro
        35                  40                  45

Ile Lys Lys Pro Asn Asn Lys Ile Leu Val Pro Lys Val Ser Gly
    50                  55                  60

Leu Gln Tyr Arg Val Phe Arg Ile His Leu Pro Asp Pro Asn Lys Phe
65                  70                  75                  80

Gly Phe Pro Asp Thr Ser Phe Tyr Asn Pro Asp Thr Gln Arg Leu Val
                85                  90                  95

Trp Ala Cys Val Gly Val Glu Val Gly Arg Gly Gln Pro Leu Gly Val
            100                 105                 110

Gly Ile Ser Gly His Pro Leu Leu Asn Lys Leu Asp Asp Thr Glu Asn
        115                 120                 125

Ala Ser Ala Tyr Ala Ala Asn Ala Gly Val Asp Asn Arg Glu Cys Ile
    130                 135                 140

Ser Met Asp Tyr Lys Gln Thr Gln Leu Cys Leu Ile Gly Cys Lys Pro
145                 150                 155                 160

Pro Ile Gly Glu His Trp Gly Lys Gly Ser Pro Cys Thr Asn Val Ala
                165                 170                 175

Val Asn Pro Gly Asp Cys Pro Pro Leu Glu Leu Ile Asn Thr Val Ile
            180                 185                 190

Gln Asp Gly Asp Met Val Asp Thr Gly Phe Gly Ala Met Asp Phe Thr
        195                 200                 205

Thr Leu Gln Ala Asn Lys Ser Glu Val Pro Leu Asp Ile Cys Thr Ser
    210                 215                 220

Ile Cys Lys Tyr Pro Asp Tyr Ile Lys Met Val Ser Glu Pro Tyr Gly
225                 230                 235                 240

Asp Ser Leu Phe Phe Tyr Leu Arg Arg Glu Gln Met Phe Val Arg His
                245                 250                 255

Leu Phe Asn Arg Ala Gly Ala Val Gly Asp Asn Val Pro Asp Asp Leu
            260                 265                 270

Tyr Ile Lys Gly Ser Gly Ser Thr Ala Asn Leu Ala Ser Ser Asn Tyr
        275                 280                 285
```

```
Phe Pro Thr Pro Ser Gly Ser Met Val Thr Ser Asp Ala Gln Ile Phe
    290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
                325                 330                 335

Thr Asn Met Ser Leu Cys Ala Ala Ile Ser Thr Ser Glu Thr Thr Tyr
            340                 345                 350

Lys Asn Thr Asn Phe Lys Glu Tyr Leu Arg His Gly Glu Glu Tyr Asp
        355                 360                 365

Leu Gln Phe Ile Phe Gln Leu Cys Lys Ile Thr Leu Thr Ala Asp Ile
370                 375                 380

Met Thr Tyr Ile His Ser Met Asn Ser Thr Ile Leu Glu Asp Trp Asn
385                 390                 395                 400

Phe Gly Leu Gln Pro Pro Gly Gly Thr Leu Glu Asp Thr Tyr Arg
                405                 410                 415

Phe Val Thr Ser Gln Ala Ile Ala Cys Gln Lys His Thr Pro Pro Ala
                420                 425                 430

Pro Lys Glu Asp Pro Leu Lys Lys Tyr Thr Phe Trp Glu Val Asn Leu
            435                 440                 445

Lys Glu Lys Phe Ser Ala Asp Leu Asp Gln Phe Pro Leu Gly Arg Lys
450                 455                 460

Phe Leu Leu Gln Ala Gly Leu Glu Ala Lys Pro Lys Phe Thr Leu Gly
465                 470                 475                 480

Lys Arg Lys Ala Thr Pro Thr Thr Ser Ser Thr Ser Thr Thr Ala Lys
                485                 490                 495

Arg Lys Lys Arg Lys Leu
                500

<210> SEQ ID NO 8
<211> LENGTH: 496
<212> TYPE: PRT
<213> ORGANISM: Artificial Sequence
<220> FEATURE:
<223> OTHER INFORMATION: Synthesized in the laboratory

<400> SEQUENCE: 8

Met Asp Ser Thr Val Tyr Val Pro Pro Asn Pro Val Ser Lys Val
1               5                   10                  15

Val Ala Thr Asp Ala Tyr Val Thr Arg Thr Asn Ile Phe Tyr His Ala
            20                  25                  30

Ser Ser Ser Arg Leu Leu Ala Val Gly His Pro Tyr Phe Ser Ile Lys
        35                  40                  45

Arg Ala Asn Lys Thr Val Val Pro Lys Val Ser Gly Tyr Gln Tyr Arg
    50                  55                  60

Val Phe Lys Val Val Leu Pro Asp Pro Asn Lys Phe Ala Leu Pro Asp
65                  70                  75                  80

Ser Ser Leu Phe Asp Pro Thr Thr Gln Arg Leu Val Trp Ala Cys Thr
                85                  90                  95

Gly Leu Glu Val Gly Arg Gly Gln Pro Leu Gly Val Gly Val Ser Gly
                100                 105                 110

His Pro Phe Leu Asn Lys Tyr Asp Asp Val Glu Asn Ser Gly Ser Gly
            115                 120                 125

Gly Asn Pro Gly Gln Asp Asn Arg Val Asn Val Gly Met Asp Tyr Lys
        130                 135                 140
```

```
Gln Thr Gln Leu Cys Met Val Gly Cys Ala Pro Leu Gly Glu His
145                 150                 155                 160

Trp Gly Lys Gly Lys Gln Cys Thr Asn Thr Pro Val Gln Ala Gly Asp
                165                 170                 175

Cys Pro Pro Leu Glu Leu Ile Thr Ser Val Ile Gln Asp Gly Asp Met
            180                 185                 190

Val Asp Thr Gly Phe Gly Ala Met Asn Phe Ala Asp Leu Gln Thr Asn
        195                 200                 205

Lys Ser Asp Val Pro Ile Asp Ile Cys Gly Thr Thr Cys Lys Tyr Pro
    210                 215                 220

Asp Tyr Leu Gln Met Ala Ala Asp Pro Tyr Gly Asp Arg Leu Phe Phe
225                 230                 235                 240

Phe Leu Arg Lys Glu Gln Met Phe Ala Arg His Phe Phe Asn Arg Ala
                245                 250                 255

Gly Glu Val Gly Glu Pro Val Pro Asp Thr Leu Ile Ile Lys Gly Ser
            260                 265                 270

Gly Asn Arg Thr Ser Val Gly Ser Ser Ile Tyr Val Asn Thr Pro Ser
        275                 280                 285

Gly Ser Leu Val Ser Ser Glu Ala Gln Leu Phe Asn Lys Pro Tyr Trp
    290                 295                 300

Leu Gln Lys Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
                325                 330                 335

Cys Ala Ser Val Thr Thr Ser Ser Thr Tyr Thr Asn Ser Asp Tyr Lys
            340                 345                 350

Glu Tyr Met Arg His Val Glu Glu Tyr Asp Leu Gln Phe Ile Phe Gln
        355                 360                 365

Leu Cys Ser Ile Thr Leu Ser Ala Glu Val Val Ala Tyr Ile His Thr
    370                 375                 380

Met Asn Pro Ser Val Leu Glu Asp Trp Asn Phe Gly Leu Ser Pro Pro
385                 390                 395                 400

Pro Asn Gly Thr Leu Glu Asp Thr Tyr Arg Tyr Val Gln Ser Gln Ala
                405                 410                 415

Ile Thr Cys Gln Lys Pro Thr Pro Glu Lys Gln Lys Pro Asp Pro Tyr
            420                 425                 430

Lys Asn Leu Ser Phe Trp Glu Val Asn Leu Lys Glu Lys Phe Ser Ser
        435                 440                 445

Glu Leu Asp Gln Tyr Pro Leu Gly Arg Lys Phe Leu Leu Gln Ser Gly
    450                 455                 460

Tyr Arg Gly Arg Ser Ser Ile Arg Thr Gly Val Lys Arg Pro Ala Val
465                 470                 475                 480

Ser Lys Ala Ser Ala Ala Pro Lys Arg Lys Arg Ala Lys Thr Lys Arg
                485                 490                 495

<210> SEQ ID NO 9
<211> LENGTH: 498
<212> TYPE: PRT
<213> ORGANISM: Artificial Sequence
<220> FEATURE:
<223> OTHER INFORMATION: Synthesized in the laboratory

<400> SEQUENCE: 9

Met Ser Asp Ser Thr Val Tyr Val Pro Pro Asn Pro Val Ser Lys
1               5                   10                  15
```

```
Val Val Ala Thr Asp Ala Tyr Val Lys Arg Thr Asn Ile Phe Tyr His
             20                  25                  30

Ala Ser Ser Ser Arg Leu Leu Ala Val Gly His Pro Tyr Tyr Ser Ile
         35                  40                  45

Lys Lys Val Asn Lys Thr Val Pro Lys Val Ser Gly Tyr Gln Tyr
 50                  55                  60

Arg Val Phe Lys Val Val Leu Pro Asp Pro Asn Lys Phe Ala Leu Pro
 65                  70                  75                  80

Asp Ser Ser Leu Phe Asp Pro Thr Thr Gln Arg Leu Val Trp Ala Cys
             85                  90                  95

Thr Gly Leu Glu Val Gly Arg Gly Gln Pro Leu Gly Val Gly Val Ser
            100                 105                 110

Gly His Pro Leu Leu Asn Lys Tyr Asp Asp Val Glu Asn Ser Gly Gly
        115                 120                 125

Tyr Gly Gly Asn Pro Gly Gln Asp Asn Arg Val Asn Val Gly Met Asp
        130                 135                 140

Tyr Lys Gln Thr Gln Leu Cys Met Val Gly Cys Ala Pro Pro Leu Gly
145                 150                 155                 160

Glu His Trp Gly Lys Gly Thr Gln Cys Ser Asn Thr Ser Val Gln Asn
                165                 170                 175

Gly Asp Cys Pro Pro Leu Glu Leu Ile Thr Ser Val Ile Gln Asp Gly
            180                 185                 190

Asp Met Val Asp Thr Gly Phe Gly Ala Met Asn Phe Ala Asp Leu Gln
        195                 200                 205

Thr Asn Lys Ser Asp Val Pro Leu Asp Ile Cys Gly Thr Val Cys Lys
210                 215                 220

Tyr Pro Asp Tyr Leu Gln Met Ala Ala Asp Pro Tyr Gly Asp Arg Leu
225                 230                 235                 240

Phe Phe Tyr Leu Arg Lys Glu Gln Met Phe Ala Arg His Phe Phe Asn
                245                 250                 255

Arg Ala Gly Thr Val Gly Glu Pro Val Pro Asp Asp Leu Leu Val Lys
            260                 265                 270

Gly Gly Asn Asn Arg Ser Ser Val Ala Ser Ser Ile Tyr Val His Thr
        275                 280                 285

Pro Ser Gly Ser Leu Val Ser Ser Glu Ala Gln Leu Phe Asn Lys Pro
290                 295                 300

Tyr Trp Leu Gln Lys Ala Gln Gly His Asn Asn Gly Ile Cys Trp Gly
305                 310                 315                 320

Asn His Leu Phe Val Thr Val Asp Thr Thr Arg Ser Thr Asn Met
                325                 330                 335

Thr Leu Cys Ala Ser Val Ser Lys Ser Ala Thr Tyr Thr Asn Ser Asp
            340                 345                 350

Tyr Lys Glu Tyr Met Arg His Val Glu Glu Phe Asp Leu Gln Phe Ile
        355                 360                 365

Phe Gln Leu Cys Ser Ile Thr Leu Ser Ala Glu Val Met Ala Tyr Ile
370                 375                 380

His Thr Met Asn Pro Ser Val Leu Glu Asp Trp Asn Phe Gly Leu Ser
385                 390                 395                 400

Pro Pro Pro Asn Gly Thr Leu Glu Asp Thr Tyr Arg Tyr Val Gln Ser
                405                 410                 415

Gln Ala Ile Thr Cys Gln Lys Pro Thr Pro Glu Lys Glu Lys Gln Asp
            420                 425                 430

Pro Tyr Lys Asp Met Ser Phe Trp Glu Val Asn Leu Lys Glu Lys Phe
```

```
                  435                 440                 445
Ser Ser Glu Leu Asp Gln Phe Pro Leu Gly Arg Lys Phe Leu Leu Gln
    450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
                485                 490                 495

Lys Lys

<210> SEQ ID NO 10
<211> LENGTH: 23
<212> TYPE: DNA
<213> ORGANISM: Artificial Sequence
<220> FEATURE:
<223> OTHER INFORMATION: Synthesized in the laboratory

<400> SEQUENCE: 10
cctcttggga tgtgcctgta tac                                            23

<210> SEQ ID NO 11
<211> LENGTH: 26
<212> TYPE: DNA
<213> ORGANISM: Artificial Sequence
<220> FEATURE:
<223> OTHER INFORMATION: Synthesized in the laboratory

<400> SEQUENCE: 11
tacaaacaca acaatagatg tatata                                         26

<210> SEQ ID NO 12
<211> LENGTH: 23
<212> TYPE: DNA
<213> ORGANISM: Artificial Sequence
<220> FEATURE:
<223> OTHER INFORMATION: Synthesized in the laboratory

<400> SEQUENCE: 12
catatgcggc ctagtgacaa tac                                            23

<210> SEQ ID NO 13
<211> LENGTH: 31
<212> TYPE: DNA
<213> ORGANISM: Artificial Sequence
<220> FEATURE:
<223> OTHER INFORMATION: Synthesized in the laboratory

<400> SEQUENCE: 13
ctcgagttac ttcctggcac gtacacgcac a                                   31
```